United States Patent
Thangapazham et al.

(10) Patent No.: US 10,478,526 B2
(45) Date of Patent: Nov. 19, 2019

(54) SKIN SUBSTITUTES AND METHODS FOR HAIR FOLLICLE NEOGENESIS

(71) Applicant: The Henry M. Jackson Foundation for the Advancement of Military Medicine, Inc., Bethesda, MD (US)

(72) Inventors: Rajesh Thangapazham, Rockville, MD (US); Thomas N. Darling, Rockville, MD (US); Shaowei Li, Potomac, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 14/888,613

(22) PCT Filed: May 1, 2014

(86) PCT No.: PCT/US2014/036351
§ 371 (c)(1),
(2) Date: Nov. 2, 2015

(87) PCT Pub. No.: WO2014/179559
PCT Pub. Date: Nov. 6, 2014

(65) Prior Publication Data
US 2016/0184481 A1     Jun. 30, 2016

Related U.S. Application Data

(60) Provisional application No. 61/819,332, filed on May 3, 2013.

(51) Int. Cl.
*A61L 27/38* (2006.01)
*A61L 27/24* (2006.01)
*A61L 27/60* (2006.01)

(52) U.S. Cl.
CPC ........... *A61L 27/3886* (2013.01); *A61L 27/24* (2013.01); *A61L 27/3804* (2013.01);
(Continued)

(58) Field of Classification Search
CPC .. A61K 31/58; A61K 31/4355; A61K 31/381; A61K 31/44; A61K 31/517;
(Continued)

(56) References Cited

U.S. PATENT DOCUMENTS 4,485,096 A   11/1984   Bell
4,919,664 A   4/1990   Oliver et al.
(Continued)

FOREIGN PATENT DOCUMENTS

JP   2001-519786 A   10/2001
JP   2004-500407 A   1/2004
(Continued)

OTHER PUBLICATIONS

Randall et al, "Stem cell factor/c-Kit signalling in normal and adrogenetic alopecia hair follicles", J. of Endocrinology (2008), 197, pp. 11-23.*
(Continued)

*Primary Examiner* — Deborah K Ware
(74) *Attorney, Agent, or Firm* — Finnegan, Henderson, Frabow, Garrett and Dunner, LLP

(57) ABSTRACT

This invention provides compositions in the form of skin substitutes comprising epithelial cells and mesenchymal cells, wherein the mesenchymal cells are not isolated from the occipital or nape region of the scalp, as well as methods for using the same.

12 Claims, 19 Drawing Sheets

(52) U.S. Cl.
CPC ........... *A61L 27/3813* (2013.01); *A61L 27/60* (2013.01); *A61L 2430/18* (2013.01)

(58) Field of Classification Search
CPC ...... A61K 31/422; A61K 31/50; A61K 31/00; A61K 31/4436; A61K 31/4184; A61K 31/435; A61K 31/438; A61K 31/496; A61K 31/4427; A61K 31/35; A61K 35/60; A61K 8/987; A61K 8/982; A61K 31/7088; A61K 35/36; A61K 38/02; A61K 45/06; A61K 8/606; A61K 8/64; A61K 8/65; A61K 8/676; A61K 8/97; A61K 8/9706; A61K 8/981; A61K 8/99; A61K 35/65; A61K 9/06; A61K 2800/805; A61K 2800/884; A61K 38/1712; A61K 38/1825; A61K 38/4893; A61K 8/4953; A61K 8/63; A61K 8/69; A61Q 19/00; A61Q 19/08; A61Q 19/004; A61Q 19/02; A61Q 19/06; A61Q 7/00; A61L 2430/18; A61L 27/24; A61L 27/3804; A61L 27/3813; A61L 27/3886; A61L 27/60; C12N 2500/32; C12N 2500/84; C12N 2501/11; C12N 2501/15; C12N 2501/70; C12N 2501/905; C12N 2533/74; C12N 5/0627; A61M 37/00; A61M 2037/0007; A45D 2200/1054; A61B 17/00491; A61B 17/54; A61B 18/203; A61B 2017/00398; A61B 2017/00495; A61B 2017/00734; A61B 2017/00747; A61B 2017/00761; A61B 2017/320004; A61B 2018/00476; A61B 2018/00577; A61H 2201/10; A61H 2201/105; A61H 2201/1215; A61H 2201/1604; A61H 2201/1671; A61H 2205/021; A61H 23/0245; A61H 7/005; A61N 2005/0644; A61N 2005/067; A61N 2005/1098; A61N 5/0617; A61N 5/10; Y10S 514/88

See application file for complete search history.

(56) References Cited

U.S. PATENT DOCUMENTS

| | | | |
|---|---|---|---|
| 5,536,656 | A | 7/1996 | Kemp et al. |
| 5,693,332 | A | 12/1997 | Hansbrough |
| 5,968,546 | A | 10/1999 | Baur et al. |
| 5,989,837 | A | 11/1999 | Allen-Hoffmann et al. |
| 6,039,760 | A | 3/2000 | Eisenberg |
| 6,815,202 | B2 | 11/2004 | Hoeffler et al. |
| 7,597,885 | B2 | 10/2009 | Barrows et al. |
| 7,985,587 | B2 | 7/2011 | Morgan et al. |
| 8,535,913 | B2 | 9/2013 | Naughton et al. |
| 2002/0120950 | A1 | 8/2002 | Hoeffler et al. |
| 2004/0068284 | A1 | 4/2004 | Barrows |
| 2005/0089512 | A1 | 4/2005 | Schlotmann et al. |
| 2005/0214344 | A1 | 9/2005 | Barrows et al. |
| 2006/0073117 | A1 | 4/2006 | Li |
| 2008/0311093 | A1* | 12/2008 | Skinner ................. A61K 8/361 424/93.21 |
| 2009/0143418 | A1 | 6/2009 | Dixon et al. |
| 2009/0280469 | A1* | 11/2009 | Jujiwara ............. C12N 5/0627 435/1.1 |
| 2014/0079686 | A1* | 3/2014 | Barman ............... A61K 8/4953 424/94.67 |
| 2014/0154326 | A1* | 6/2014 | Guo .................... C12N 5/0698 424/490 |
| 2015/0268254 | A1* | 9/2015 | Guasch ................ C12N 5/0625 435/6.12 |

FOREIGN PATENT DOCUMENTS

| | | |
|---|---|---|
| JP | 2007-274949 | 10/2007 |
| JP | 2007-274949 A | 10/2007 |
| WO | WO 91/16010 A1 | 10/1991 |
| WO | WO 98/43661 A1 | 10/1995 |
| WO | WO 2000/29553 A1 | 5/2000 |
| WO | WO 2001/74164 A1 | 10/2001 |
| WO | WO 2003/055990 A2 | 7/2003 |
| WO | WO 2006/097701 A2 | 9/2006 |
| WO | WO 2009/118283 A1 | 10/2009 |
| WO | WO 2011/160055 A2 | 12/2011 |
| WO | WO 2012/115079 A1 | 8/2012 |

OTHER PUBLICATIONS

Anjum, R. and J. Blenis (Oct. 2008) "The RSK family of kinases: emerging roles in cellular signalling" *Nat. Rev. Mol. Cell Biol.*, 9:747-758.

Asbill, C. et al. (2000) "Evaluation of a Human Bio-Engineered Skin Equivalent for Drug Permeation Studies" *Pharmaceutical Research*, 17(9):1092-1097.

Auger, F.A. et al. (Feb. 2000) "Multistep Production of Bioengineered Skin Substitutes: Sequential Modulation of Culture Conditions" *In Vitro Cell. Dev. Biol.—Animal*, 36:96-103.

Baba, M. et al. (Oct. 2006) "Folliculin encoded by the BHD gene interacts with a binding protein, FNIP1, and AMPK, and is involved in AMPK and mTOR signaling" *PNAS*, 103(42):15552-15557.

Baden, H.P. et al. (Mar. 1987) "Isolation and Characterization of a Spontaneously Arising Long-Lived Line of Human Keratinocytes (NM 1)" *In Vitro Cell. Dev. Biol.*, 23(3 Pt. 1):205-213.

Biernaskie, J.A. (2006) "Isolation of skin-derived precursors (SKPs) and differentiation and enrichment of their Schwann cell progeny" *Nature Protocols*, 1(6):2803-2612.

Blumenthal, G.M. and P.A. Dennis (2008) "PTEN hamartoma tumor syndromes" *Eur. J. Human Genet.*, 16:1289-1300.

Boukamp, P. et al. (1988) "Normal Keratinization in a Spontaneously Immortalized Aneuploid Human Keratinocyte Cell Line" *J. Cell Biol.*, 106:761-771.

Brummelkamp, T.R. et al. (2003) "Loss of the cylindromatosis tumour suppressor inhibits apoptosis by activating NF-κB" *Nature*, 424:797-801.

Burgstaller, S. and M. Rosner (Feb. 2009) "Tuberin, p27 and mTOR in different cells" *Amino Acids*, 36(2):297-302 (Abstract, 8 pages).

Carretero, M. et al. (Jul./Aug. 2011) "Applicability of bioengineered human skin: From preclinical skin humanized mouse models to clinical regenerative therapies" *Bioengineered Bugs*, 2(4):203-207.

Castilho et al. (Sep. 2009) "mTOR Mediates Wnt-Induced Epidermal Stem Cell Exhaustion and Aging" *Cell Stem Cell*, 5(3):279-289. NIH Public Access Author Manuscript; available in PMC Sep. 15, 2010 (25 pages).

Chang, H-C. et al. (Aug. 1982) "Human amniotic fluid cells grown in a hormone-supplemented medium: Suitability for prenatal diagnosis" *Proc. Natl. Acad. Sci. USA*, 79:4795-4799.

Chuong, C-M. et al. (2007) "Defining Hair Follicles in the Age of Stem Cell Bioengineering" *J. Invest. Dermatol.*, 127:2098-2100.

Clements et al. (2009) "Analysis of the oestrogen response in an angiomyolipoma derived xenograft model" *Endocrine-Related Cancer*, 16:59-72.

Dan, H.C. and A.S. Baldwin (2008) "Differential Involvement of IκB Kinases α and β in Cytokine- and Insulin-Induced Mammalian Target of Rapamycin Activation Determined by Akt" *J. Immunol.*, 180:7562-7589.

Darling, T.N. (2006) "Hitting the Mark in Hamartoma Syndromes" *Adv. Dermatol.*, 22:181-200.

Dere, R. et al. (Feb. 2010) "Carboxy Terminal Tail of Polycystin-1 Regulates Localization of TSC2 to Repress mTOR" *PLoS ONE*, 5(2):e9239.

Dibella, L.M.. et al. (2009) "Zebrafish Tsc1 reveals functional interactions between the cilium and the TOR pathway" *Hum. Mol. Genet.*, 18(4):595-606.

Downward, J. (2003) "Targeting RAS Signalling Pathways in Cancer Therapy" *Nat. Rev. Cancer*, 3:11-22.

(56) References Cited

OTHER PUBLICATIONS

Düvel, K. et al. (Jul. 2010) "Activation of a Metabolic Gene Regulatory Network Downstream of mTOR Complex 1" *Mol. Cell*, 39:171-163.

Edwards, H. et al. (2009) "RUNX1 regulates phosphoinositide 3-kinase/AKT pathway: role in chemotherapy sensitivity in acute megakaryocytic leukemia" *Blood*, 114(13):2744-2752.

Ehama, R. et al. (2007) "Hair Follicle Regeneration Using Grafted Rodent and Human Cells" *J. Invest. Dermatol.*, 127:2106-2115.

Endersby, R. and S.J. Baker (2008) "PTEN signaling in brain: neuropathology end tumorigenesis" *Oncogene* 27:5415-5430.

European Patent Application No. 11796538.4, by The Henry M. Jackson Foundation for the Advancement of Military Medicine, Inc.: Extended European Search Report. including Supplementary Search Report and Opinion, dated Nov. 22, 2013 (8 pages).

Falanga, V. and M. Sabolinski (Jul./Aug. 1999) "A bilayered living skin construct (APLIGRAF®) accelerates complete closure of hard-to-heal venous ulcers" *Wound Rep. Reg.* 7:201-207.

Galbaugh, T. et al.. (Sep. 2006) "EGF-induced activation of Akt results in mTOR-dependent p70S6 kinase phosphorylation and inhibition of HCII cell lactogenic differentiation" *BMC Cell Biol.*, 7:34. [online] doi.10.1186/1471-2121-7-34 (15 pages).

Gharzi, A. et al, (2003) "Plasticity of Hair Follicle Dermal Cells in Wound Healing and Induction" *Exp. Dermatol.*, 12(2):e126-136.

Greenberg, S. et al. (2005) "In Vivo Transplantation of Engineered Human Skin" *Methods Mol. Biol.*, 289:425-429.

Handel, E-M. and T. Cathomen (2011) "Zinc-Finger Nuclease Based Genome Surgery: It's All About Specificity" *Curr. Gene Ther.*, 11:28-37.

Hardy, M.H. (Feb. 1992) "The Secret Life of the Hair Follicle" *TIG*, 8(2):55-61.

Hasumi, Y. et al. (Nov. 2009) "Homozygous loss of BHD causes early embryonic lethality and kidney tumor development with activation of mTORC1 and mTORC2" *PNAS*, 106(44):18722-18727.

Havlickova, B. et al. (2004) "Towrads optimization of an organotypic assay system that imitates human hair follicle-like epithelial-mesenchymal interactions" *Br. J. Dermatol.*, 151:753-765.

Hay, N. and N. Sonenberg (2004) "Upstream and downstream of mTOR" *Genes Dev.*, 18:1926-1945.

Headington, J.T. (1987) "Hair Follicle Bioiogy and Topical Minoxidil: Possible Mechanisms of Action" *Dermatologica*,: 175(Suppl. 2):19-22.

Holt, N. et al. (Aug. 2010) "Zinc finger nuclease-mediated CCR5 knockout hematopoetic stem cell transplantation controls HIV-1 in vivo" *Nat. Biotechnol.*, 28(8):839-847, NIH Public Access Author Manuscript, available in PMC Apr. 21, 2011.

Hong, F. et al. (Jun. 2008) "rnTOR-Raptor Binds and Activates SGK1 to Regulate p27 Phosphorylation" *Mol. Cell*, 30:701-711.

Huang, Y-C. et al. (2013) "Scalable production of controllable dermal papilla spheroids on PVA surfaces and the effects of spheroid size en hair follicle regeneration" *Biomaterials*, 34:442-451.

Inoki, K. et al. (Sep. 2002) "T3C2 is phosphorylated and inhibited by Akt and suppresses mTOR signalling" *Nat. Cell Biol.*, 4:648-657.

Inoki, K. et al. (2003) "Rheb GTPase is a direct target of TSC2 GAP activity and regulates mTOR signaling" *Genes Dev.*, 17:1829-1834.

Inoue, K. et al. (2009) "Evaluation of Animal Models for the Hair-Inducing Capacity of Cultured Human Dermal Papilla Cells" *Cells Tissues Organs*, 190:102-110.

International Search Report and Written Opinion issued in PCT/US2011/040937, dated Mar. 8, 2012 (8 pages).

International Search Report and Written Opinion issued in PCT/US2014/036351, dated Jul. 24, 2015 (12 pages).

Jahoda, C.A.B. et al. (1993) "Induction of Hair Growth in Ear Wounds by Cultured Dermal Papilla Cells" *J. Invest. Dermatol.*, 101:564-590.

Johannessen, C.M. et al. (Jun. 2005) "The NF1 tumor suppressor critically regulates TSC2 and mTOR" *PNAS*, 102(24):8573-8578, with Correction in *PNAS*, 102(44):16119-16120 (Nov. 2005).

Kamsteeg, M. et al. (May 2011) "Type 2 Helper T-Cell Cytokines Induce Morphologic and Molecular Characteristics of Atopic Dermatitis in Human Skin Equivalent" *Am. J. Pathol*, 178(5):2091-2099.

Kang, B.M. et al. (2012) "Sphere Formation Increases the Ability of Cultured Human Dermal Papilla Cells to Induce Hair Follicles from Mouse Epidermal Cells in a Reconstitution Assay" *J. Invest. Dermatol*, 132: 237-239.

Kim, Y.S. et al: (1999) "Stable overexpression of MEN1 suppresses tumorigenicity of RAS" *Oncogene*, 18:5936-5942.

Kishimoto, J. et al. (2000) "Wnt signaling maintains the hair-inducing activity of the dermal papilla" *Genes & Development*, 14:1181-1185.

Koseoglu, S. et al. (2007) "AKT1, AKT2 and AKT3-Dependent Cell Survival is Cell Line-Specific and Knockdown of All Three Isoforms Selectively Induces Apoptosis in 20 Human Tumor Cell Lines" *Cancer Biol. & Ther.*, 6(5):755-762.

Laderoute, K.R. (Jul. 2010) "SU11248 (sunitinib) directly inhibits the activity of mammalian 5'-AMP-activated protein kinase (AMPK)" *Cancer Biol. Ther.*, 10(1):1-8.

Ledford, H. (Mar. 2011) "Targeted gene editing enters clinic," *Nature*, 471:16.

Lee, H.J. et al. (2010) "Targeted chromosomal deletions in human cells using zinc finger nucleases" *Genome Res.*, 20;81-89.

Lee, D-F. et al. (Aug. 2007) "IKKβ Suppression of TSC1 Links Inflammation and Tumor Angiogenesis via the mTOR Pathway" *Cell*, 130:440-455.

Lee, D.F. et al. (2008) "IKKβ suppression of TSC1 function links the mTOR pathway with insulin resistance" *Int'l J. Mol. Med.*, 22:533-638.

Li et ai. (Aug. 2005) "MCP-1 overexpressed in tuberous sclerosis lesions acts as a paracrine factor for tumor development" *J. Exp. Med.*, 202(5):617-624.

Li, S. et al. (Mar. 2008) "Mesenchymal-epithelial interactions involving epireguiin in tuberous sclerosis complex hamartomas" *PNAS*, 105(9);3539-3544.

Li, S. et al. (Mar. 2011) "Human TSC2-null fibroblast-like cells induce hair follicle neogeneisis and hamartoma morphogenesis" *Nature Commun.*, 2:Article 235.

Lin et al. (2008) "Microencapsulated Human Hair Dermal Papilla Cells: A Substitute for Dermal Papilla?" *Arch Dermatol. Res.*, 300:531-535.

Linehan, W.M. et al. (2010) "Molecular Diagnosis and Therapy of Kidney Cancer" *Annu. Rev. Med.*, 81:329-343, NIH Public Access Author Manuscript, available in PMC Jan. 1, 2011 (18 pages).

Long, X. et al. (Apr. 2005) "Rheb Binds and Reguiates the mTOR Kinase" *Curr. Biol.*, 15:702-713.

Ma, X.M. et al. (Apr. 2008) "SKAR Links Pre-mRNA Splicing to mTOR/S6K1-Mediated Enhanced Translation Efficiency of Spliced mRNAs" *Cell*, 133:303-313.

McNicholas, C.M. and K.H. Berecek (2009) "Mammalian Target of Rapamycin: MasTOR Mediator of Cellular Changes in Pathological States?" *Hypertension*, 54;1221-1222.

Meana et al. (1998) "Large Surface of Cultured Human Epithelium Obtained on a Dermal Matrix Based on Live Fibroblast-Containing Fibrin Gels" *Burns*, 24:621-630.

Mendoza et al. (Jun. 2011) "The Ras-ERK and PI3K-mTOR Pathways: Cross-talk and Compensation" *Trends Biochem. Sci.*, 36(6):320-328 NIH Public Access Author Manuscript, available in PMC Jun. 1, 2012 (18 pages).

Metcalfe, A.D. and M.W.J, Ferguson (2007) "Tissue engineering of replacement skin: the crossroads of biomaterials, wound healing, embryonic development, stem cells and regeneration" *J.R. Soc. Interface*, 4:413-437.

Mullally, A and B.L. Ebert (2010) "NF1 Inactivation Revs Up Ras in Adult Acute Myelogenous Leukemia" *Clin. Cancer Res.*, 16:4074-4076.

Nagy, A. et al. (2004) "Lack of mutation of the folliculin gene in sporadic chromophobe renal cell carcinoma and renal oncocytoma" *Int. J. Cancer* 109(3):472-475.

Nowak et al. (Jul. 2008) "Hair Follicle Stem Cells Are Specified and Function in Early Skin Morphogenesis" *Cell Stem Cell*, 3:33-43.

(56) References Cited

OTHER PUBLICATIONS

O'Callaghan, F. (2007) "Tuberous sclerosis complex" *Paediatrics and Child Health*, 18(1):30-36.
Ohyama et al. (2010) "The Mesenchymal Component of Hair Follicle Neogenesis: Background, Methods and Molecular Characterization" *Exp. Dermatol.*, 19:89-99.
Ohyama, M. et al. (May 2012) "Restoration of the intrinsic properties of human dermal papilla in vitro" *J. Cell Sci.*, 125:4114-4125.
Ohyama et al. (2013) "Strategies to Enhance Epithelial-Mesenchymal Interactions for Human Hair Follicle Bioengineering" *J. Dermatol. Sci.*, 70:78-87.
Ortiz-Urda, S. et al. (2003) "Injection of Genetically Engineered Fibroblasts Corrects Regenerated Human Epidermolysis Bullosa Skin Tissue" *J. Clin. Invest.*, 111(2):251-255.
Peterson, T.R. et al, (May 2009) "DEPTOR Is an mTOR Inhibitor Frequently Overexpressed in Multiple Myeloma Cells and Required for Their Survival" *Cell*, 137(5):873-886.
Portsmann, T. et al, (Sep. 2008) "SREBP Activity Is Regulated by mTORC1 and Contributes to Akt-Dependent Cell Growth" *Cell Metab.*, 8:224-236.
Proud, C.G. (2009) "DynarniC Balancing: DEPTOR Tips the Scales" *J. Mol. Cell Biol.*, 1(2):61-63.
Qiao, J. et al. (2009) "Hair Follicle Neogenesis Induced by Cultured Human Scalp Dermal Papilla Cells" *Regen. Med.*, 4(5)•667-676.
Ravitz, M.J. et al. (2007) "c-myc Repression of TSC2 Contributes to Control of Translation Initiation and Myc-Induced Transformation" *Cancer Res.*, 67:11209-11217.
Reddy, S. et al. (2001) "Characterization of Wnt Gene Expression in Developing and Postnatal Hair Follicles and Identification of Wnt5a as a Target of Sonic Hedgehog in Hair Follicle Morphogenesis" *Mech Dev.*, 107(1-2):69-82.
Reynolds, A.J. et al. (Nov. 1999) "Trans-gender induction of hair follicles" *Nature*, 402:33-34.
Richardson, C.J. et al. (Sep. 2004) "SKAR Is a Specific Target of S6 Kinase 1 in Cell Growth Control" *Curr. Biol.*, 14:1540-1549.
Rommel, C. et al. (Nov. 2001) "Mediation of IGF-1-induced skeletal myotube hypertrophy by PI(3)K/Akt/mTOR and PI(3)K/Akt/GSK3 pathways" *Nature Cell Biol.*, 3:1009-1013.
Roux, P.P. et al. (Sep. 2004) "Tumor-promoting phorbol esters and activated Ras inactivate tne tuberous sclerosis tumor suppressor complex via p90 ribosomal S6 kinase" *PNAS*, 101(37):13439-13494.
Sansal, I. and W.R. Sellers (Jul. 2004) "The Biology and Clinical Relevance of the PTEN Tumor Suppressor Pathway" *J. Clin. Oncol.*, 22(14):2954-2963.
Scaife, M.D. et al. (2009) "Novel Application of Lentiviral Vectors Towards Treatment of Graft-Versus-Host Disease" *Expert Opin. Biol. Ther.* 9(6):749-761.
Schmidt, E.V. et al. (May 2009) "Growth Controls connect. Interactions between c-myc and the tuberous sclerosis complex-mTOR pathway" *Cell Cycle*, 8(9):1344-1351.
Selman, C. et al. (Oct. 2009) "Ribosomal Protein S6 Kinase 1 Signaling Regulates Mammalian Life Span" *Science*, 326:140-144, with Erratum posted Oct. 7, 2011.
Shakhova, O. and L. Sommer (2010) "Neural Crest-Derived Stem Cells" StemBook, The Stem Cell Research Community [online]. Retrieved from: http://www.stembook.org/node/696, on Oct. 21, 2015 (24 pages).
Sherr, A.E. and E.A. Vitals (1963) "Quaternary antistatic agents effective in plastics" *I & EC Product Research and Development*, 2(2):97-102.
Shevchenko, R.V. et al. (2010) "A Review of Tissue-Engineereed Skin Bioconstructs Available for Skin Reconstruction" *J.R. Soc. Interface*, 7:229-258.
Shimizu, H. and B.A. Morgan (2004) "Wnt Signaling through the β-Catenin Pathway Is Sufficient to Maintain, but Not Restore, Anagen-Phase Charecteristics of Dermal Papilla Cells" *J. Invest Dermatol*, 122:239-245.

Squarize, C.H. et al. (May 2010) "Accelerated Wound Healing by mTOR Activation in Genetically Defined Mouse Models" *PloS ONE*, 5(5):e10643 (10 pages).
Sriwiriyanont, P. et al. (2012) "Morphogenesis of chimeric hair follicles in engineered skin substitutes with human keratinocytes and murine dermal papilla cells" *Exp. Dermatol.*, 21:783-801.
Testa, J.R. and P.N. Tsichlis (2005) "AKT signaling in normal and malignant cells" *Oncogene*, 24:7391-7393.
Thomas, G. (2002) "The S6 kinase Signaling Pathway in the Control of Development and Growth" *Biol. Res.*, 35(2):305-313. [online] Retrieved from: http://dx.doi.org/10.4067/S0716-97502002000200022, on May 12, 2014 (8 pages).
Van Der Loos, C.M. (2008) "Multiple Immunoenzyme Staining: Methods and Visualizations for the Observation With Spectral Imaging" *J. Histochem. Cytochem.*, 56(4):313-328.
Van Steensel, M.A.M. et al. (2009) "Molecular pathways involved in hair follicle tumor formation: all about mammalian target of rapamycin?" *Exp. Dermatol.*, 18:188-191.
Vander Haar, E. et al. (2007) "Insulin signalling to mTOR mediated by the Akt/PKB substrate PRAS40" *Nature Cell Biol.*,9(3):316-323, with Supplementary Information (6 pages).
Veves, A. et al. (2001) "Graftskin, a Human Skin Equivalent, Is Effective in the Management of Noninfected Neuropathic Diabetic Foot Ulcers" *Diabetes Care*, 24:290-295.
Vogler, I. et al. (Jul. 2010) "An Improved Bicistronic CD20/tCD34 Vector for Efficient Purification and In Vivo Depletion of Gene-Modified T Cells for Adoptive Immunotherapy" *Molecular Therapy*, 18(7):1330-1338; published online May 11, 2010.
Wagner, A.J. et al. (Feb. 2010) "Clinical Activity of mTOR Inhibition With Sirolimus in Malignant Perivascular Epithelioid Cell Tumors: Targeting the Pathogenic Activation of mTORC1 in Tumors" *J. Clin. Oncol.*; 28(5);835-840.
Wang, L. et al. (Jun. 2008) "Regulation of Proline-rich Akt Substrate of 40 kDa (PRAS40) Function by Mammalian Target of Rapamycin Complex 1 (mTORC1)-mediated Phosphorylation" *J. Biol. Chem.*, 283(23):15619-15627.
Weill, C.O. et al. (2008) "A practical approach for intracellular protein delivery" *Cytotechnology*, 56:41-48.
Yang, Q. and K-L. Guan (2007) "Expanding mTOR signaling" *Cell Res.*, 17:666-681.
Young, T-H, et al. (2008) "Self-assembly of dermal papitla cells into inductive spheroidal microtissues on poly(ethylene-co-vinyl alcohol) membranes for hair follicle regeneration" *Biomaterials*, 29:3521-3530.
Zhang, C. and X. Fu (2008) "Therapeutic potential of stem cells in skin repair and regeneration" *Chinese J. Traumatol.*, 11(4); 209-221.
Zhang, H.H. et al. (Jul. 2009) "Insulin Stimulates Adipogenesis through the Akt-TSC2-mTORC1 Pathway" *PLoS ONE*, 4(7):e6189 (14 pages).
Zhang, H. et al. (Oct. 2003) "Loss of Tsc1/Tsc2 activates mTOR and disrupts PI3K-Akt signaling through downregulation of PDGFR" *J. Clin. Invest.*, 112(8):1223-1233.
Zhang, H.H. et al. (Oct. 2006) "S6K1 Regulates GSK3 under Conditions of mTOR-Dependent Feedback Inhibition of Akt" *Mol. Cell.*, 24:185-197.
Zheng, Y. et al. (2005) "Organogenesis From Dissociated Cells: Generation of Mature Cycling Hair Follicles From Skin-Derived Cells" *J. Invest. Dermatol.*, 124:867-876.
U.S. Appl. No. 13/704,431, filed Feb. 26, 2013, by Thangapazham et al.: Non-Final Office Action, dated Jul. 11, 2014 (11 pages).
U.S. Appl. No. 13/704,431, filed Feb. 26, 2013, by Thangapazharn et al.: Non-Final Office Action, dated Jan. 22, 2016 (10 pages).
U.S. Appl. No. 13/704,431, filed Feb. 26, 2013, by Thangapazham et al.: Non-Final Office Action, dated Aug. 25, 2015 (11 pages).
Yamauchi et al., "Inhibition of glycogen synthase kinase-3 enhances the expression of alkaline phosphatase and insulin-like growth factor-1 in human primary dermal papilla cell culture and maintains mouse hair bulbs in organ culture," Arch Dermatol Res. (2009) 301:357-365.
Dotto et al., "Transformation of murine melanocytes by basic fibroblast growth factor cDNA and oncogenes and selective sup-

(56) References Cited

OTHER PUBLICATIONS pression of the transformed phenotype in a reconstituted cutaneous environment," J Cell Biol. (1989) 109:3115-3128.

Gandarillas et al., "c-Myc promotes differentiation of human epidermal stem cells," Genes Dev. (1997) 11(21):2869-2882.

Yoshioka et al., "WNT7A regulates tumor growth and progression in ovarian cancer through the Wnt/β-catenin pathway," Mol Cancer Res. (2012) 10(3):469-482.

Ochoa-Hernández et al., "Peripheral T-lymphocytes express WNT7A and its restoration in leukemia-derived lymphoblasts inhibits cell proliferation," BMC Cancer (2012) 12:60.

McCubrey et al., "Effects of mutations in Wnt/β-catenin, hedgehog, Notch and PI3K pathways on GSK-3 activity-Diverse effects on cell growth, metabolism and cancer," Biochim Biophys Acta. (2016) 1863(12):2942-2976.

Arbiser et al., "The generation and characterization of a cell line derived from a sporadic renal angiomyolipoma: use of telomerase to obtain stable populations of cells from benign neoplasms," Am J Pathol. (2001) 159(2):483-449.

Scandurro et al., "Immortalized rat whisker dermal papilla cells cooperate with mouse immature hair follicle buds to activate type IV procollagenases in collagen matrix coculture: correlation with ability to promote hair follicle development in nude mouse grafts," J Invest Dermatol (1995) 105:177-183.

Yang et al., "Review of hair follicle dermal cells," J. Dermatological Science (2009) 57:2-11.

Zhao et al., "Treatment of alopecia by transplantation of hair follicle stem cells and dermal papilla cells encapsulated in alginate gels," Medical Hypotheses (2008) 70:1014-1016.

Fuchs et al., "More than one way to skin . . . ," Genes & Development (2008) 22:976-985.

Final Office Action dated Jun. 24, 2016, in U.S. Appl. No. 13/704,431, 10 pages.

Non-Final Office Action dated Jun. 29, 2017, in U.S. Appl. No. 13/704,431, 10 pages.

Krugluger et al., "Reorganization of hair follicles in human skin organ culture induced by cultured human follicle-derived cells," Exp. Dermatol., 2005, 14:580-585.

Limat et al., "Experimental modulation of the differentiated phenotype of keratinocytes from epidermis and hair follicle outer root sheath and matrix cells," Annals New York Academy of Sciences, 1991, 642:125-147.

Kaur, "Hair-follicle dermal papilla and sheath fibroblasts provide a supportive microenvironment for human skin regeneration," Br. J. Dermatol., 2017, 176:1123-1124.

Webb et al., "The cutaneous features of tuberous sclerosis: a population study," Br. J. Dermatol., 1996, 135:1-5.

Non-Final Office Action dated Jun. 28, 2018, in U.S. Appl. No. 13/704,431, 60 pages.

* cited by examiner

Human-specific anti-COX IV

Fig. 6
Fig. 6A 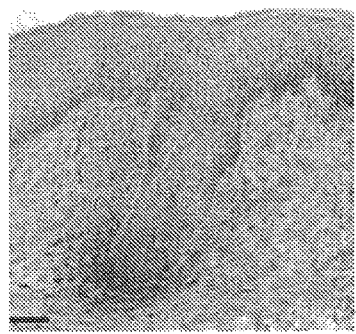 Fig. 6B 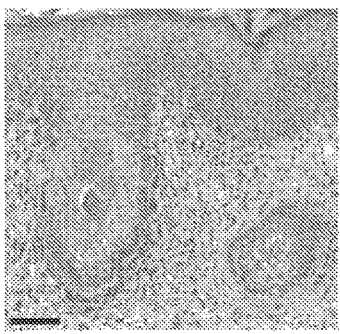 Fig. 6C 
Alkaline Phosphatase    Nestin    Versican Ki-67

Fig. 8
Fig. 8A
Fig. 8B
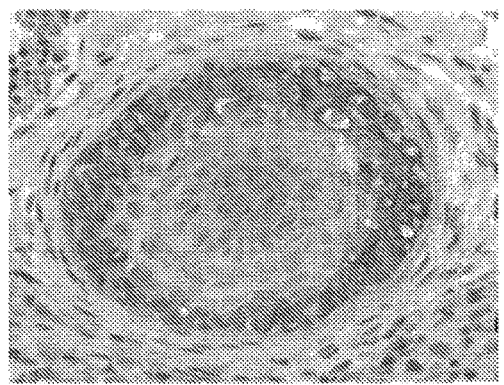
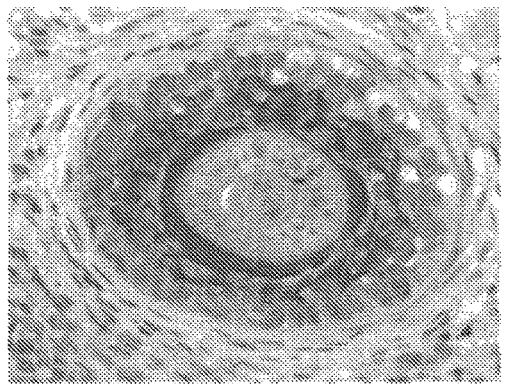
Keratin 15          Keratin 75

Primary Keratinocytes

Passage 1 keratinocytes

Passage 3 keratinocytes

Fig. 11

| Keratinocyte Passage | Number of grafts with hair follicle / total number of grafts | Hair follicles/ mm of epidermis | Hair follicle Diameter in µm |
|---|---|---|---|
| Primary | 6/6 | 0.94±0.44 | 240±37** |
| Passage 1 | 5/6 | 0.82±0.55 | 144±26 |
| Passage 3 | 5/7 | 0.24±0.18* | 106±22 |

FIG. 16A
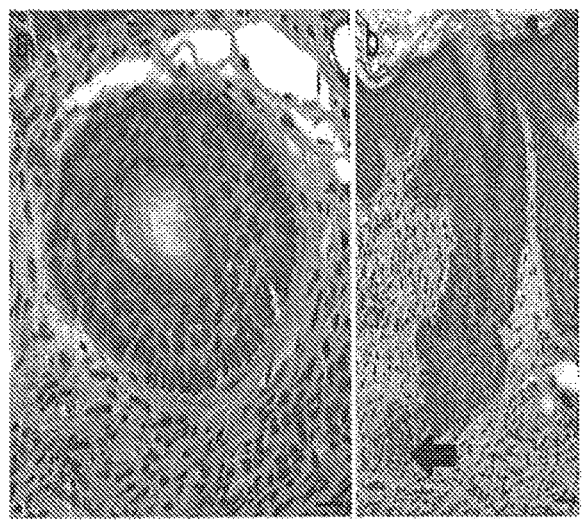
FIG. 16B
FIG. 16C
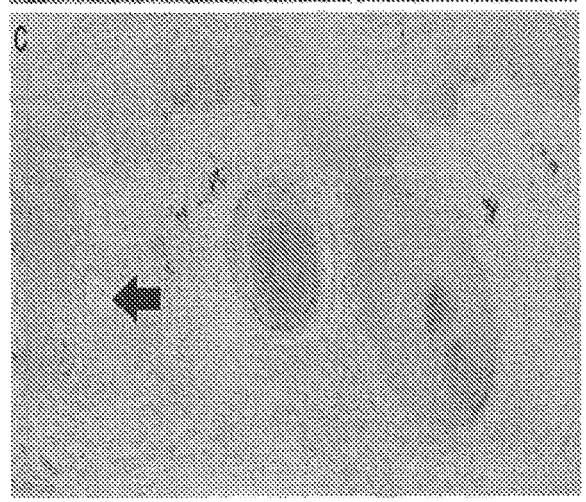

FIG. 17A
FIG. 17B
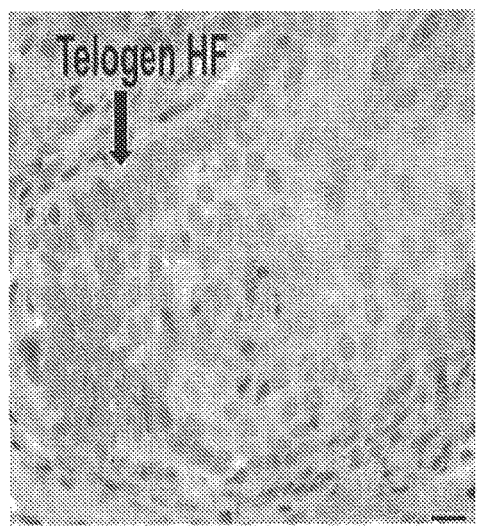
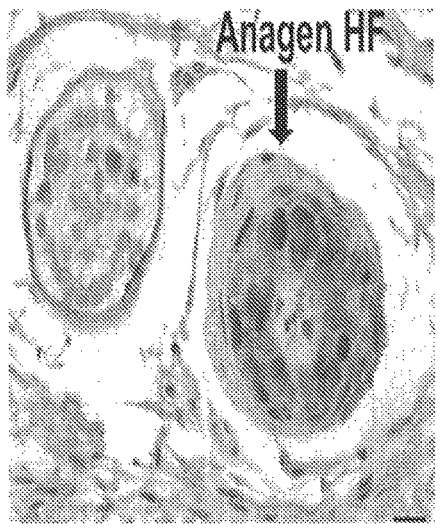

SKIN SUBSTITUTES AND METHODS FOR HAIR FOLLICLE NEOGENESIS

CROSS-REFERENCE TO RELATED APPLICATIONS

This application is the United States national stage entry under 35 U.S.C. § 371 of International Application No. PCT/US2014/036351, filed May 1, 2014 and published as WO 2014/179559 A1, which claims priority to U.S. Provisional Application No. 61/819,332, filed May 3, 2013. The contents of these applications are each incorporated herein by reference in their entirety.

STATEMENT OF GOVERNMENT INTEREST

This invention was made with government support under Grant No. CA122963 awarded by the National Institutes of Health. The government has certain rights in the invention.

FIELD OF THE INVENTION

The present invention relates to compositions in the form of skin substitutes and microspheres comprising neural crest-derived mesencymal cells, such as hair follicle dermal cells, e.g., dermal papilla ("DP") cells, or dermal sheath cells, that are capable of inducing hair follicles ("HFs"). The present invention also relates to methods, uses, and compositions for inducing HF growth and neogenesis. In some embodiments, the present invention can be used for the treatment of full- or partial-thickness skin loss, wounds, burns, scars, and full- or partial-hair loss.

BACKGROUND AND SUMMARY

Studies of hair and skin continue to be at the forefront of regenerative medicine. Skin substitutes were among the earliest products to be developed using principles of tissue engineering, and the success of these ventures is evident in the clinical use of several commercially available products. In addition, hair restoration is one of the fastest growing areas of cosmetic therapies for both men and women.

The current clinical "gold standard" for treating major skin injuries involves the use of split-thickness skin autografts, which involves transplanting the epidermis with a portion of the dermis from one location on a patient to another. In cases where there is insufficient donor skin to cover the wounds, however, skin substitutes may be used. Skin substitutes available today have varied compositions, but generally comprise a nonliving collagen matrix and different combinations of keratinocytes and fibroblasts. For example, APLIGRAF® (Organogenesis, Inc., Canton, Mass.), which is reported to be the most clinically successful composite skin substitute currently available, is composed of allogeneic neonatal fibroblasts in bovine type I collagen overlaid with allogeneic neonatal keratinocytes.

However, currently available skin substitutes cannot perform all the functions of normal skin. For example, hair follicle (HF) neogenesis is not observed using any currently available skin substitute, which limits their use in patients. HFs and their associated sebaceous glands are important for appearance, skin hydration, barrier formation, and protection against pathogens. In addition, HFs store epidermal stem cells that may be called upon during wound healing. Thus, skin with HFs heals more rapidly than skin without HFs. In addition, any stem cells that might exist in skin lacking HFs are located in superficial layers of the epidermis, making the cells susceptible to loss through minor trauma and damage through ultraviolet light. Thus, treatments that involve neogenesis of normal HFs would find much wider application for restoring normal skin function and appearance.

During embryogenesis, mesenchymal cells signal the overlying epithelium to induce HF formation, and in adults a specialized group of mesenchymal cells, the dermal papilla (DP) cells, have been shown to retain the capacity to induce HF regeneration (Hardy 1992, Reddy et al., 2001, Gharzi et al., 2003). DP cells from rodents induce HFs in a variety of assays (reviewed in Ohyama et al., 2009), but it has been difficult to grow human DP cells that maintain inductive capacity in culture (Ohyama et al., 2013). This is a significant problem since DP cells must be enriched in culture to expand the cells needed for successful clinical use. Recent technological advances have enabled the use of human cells to form chimeric HFs, for example by combining human keratinocytes and rodent mesenchymal cells in chamber assays (Ehama et al., 2007), by combining human scalp dermal papilla cells and mouse epidermal keratinocytes in flap grafts (Qiao et al., 2009), or by injecting human DP cells, grown as spheroids, together with mouse epidermal cells in reconstitution or "patch" assays (Kang et al., 2012).

However, while chimeric HFs are highly valuable as investigative tools, they lack clinical utility because the HFs produced by these methods are not fully human constructs (but instead are chimeric rodent/human constructs), are not completely developed, contain hair shafts in the wrong anatomical location, do not exhibit long-term graft survival and normal HF cycling, and/or do not form HFs that contain sebaceous glands. In addition, HFs produced by such methods tend to grow in variable and uncontrollable directions, resulting in unnatural looking hair. Thus, the follicles produced by such methods are not useful for human HF neogenesis in skin lacking hair follicles.

Thus, a need exists for methods and compositions capable of generating morphologically-correct, fully-developed, non-immunogenic human hair follicles. Such methods and compositions would be useful for treating conditions such as full- or partial-thickness skin loss, wounds, burns, scars, and hair loss. The present invention fills these needs by providing cellular compositions capable of hair growth, neogenesis, and regeneration.

The present invention provides compositions in the form of skin substitutes and microspheres comprising neural crest-derived mesencymal cells, wherein the skin substitute is capable of inducing hair follicles that are morphologically-correct and are useful in any application requiring hair follicle formation/neogenesis, or in any condition where hair follicle formation/neogenesis is desired.

In one embodiment, the skin substitute or microsphere comprises neural crest-derived mesenchymal cells. In some embodiments, the skin substitute or microsphere further comprises epithelial cells, optionally with collagen. In another embodiment, the skin substitute or microsphere comprises scalp- or face-derived mesenchymal cells and epithelial cells, optionally with collagen. In another embodiment, the skin substitute or microsphere comprises epithelial cells and scalp- or face-derived mesenchymal cells, wherein the mesencymal cells are neural crest-derived, optionally with collagen. In yet another embodiment, the skin substitute or microsphere comprises epithelial cells and hair follicle dermal cells, optionally with collagen. In some aspects the epithelial cells are keratinocytes. In some aspects the skin substitute comprises cells of human origin only.

In various embodiments, a skin substitute is provided, comprising isolated neural crest-derived mesenchymal cells and/or epithelial cells. In some embodiments, the epithelial cells are keratinocytes, and/or the mesenchymal cells are hair follicle dermal cells (e.g., one or more of dermal papilla cells, dermal sheath cells, or hair follicle dermal cells derived from scalp or face). In some embodiments, the hair follicle dermal cells are derived from frontal, temporal, mid scalp, top of head, vertex, or parietal region of the scalp. In some embodiments, the hair follicle dermal cells are not derived from an occipital or nape region of the scalp. In various embodiments, the skin substitutes described above contain epithelial cells and neural crest-derived mesenchymal cells from a human. In some embodiments, the skin substitutes further comprise collagen. In some embodiments, the keratinocytes or keratinocyte-like cells are induced pluripotent stem (iPS) cells differentiated into keratinocytes or keratinocyte-like cells. In some embodiments, the mesenchymal cells and epithelial cells are taken from the same donor and/or the same body regions of a donor (e.g., the mesenchymal cells and epithelial cells are taken from tissue in the same donor region, e.g., keratinocytes and mesenchymal cells from the frontal scalp). In some embodiments, the mesenchymal cells and epithelial cells are taken from different donors and/or different body regions of a donor (e.g., the mesenchymal cells and epithelial cells are not taken from tissue in the same donor region, e.g., keratinocytes and mesenchymal cells from the frontal scalp).

In various embodiments, a skin substitute is provided, comprising epithelial cells and hair follicle dermal cells, wherein the hair follicle dermal cells are not derived from an occipital or nape region of the scalp. In some embodiments, the epithelial cells are keratinocytes, and/or the mesenchymal cells are hair follicle dermal cells (e.g., one or more of dermal papilla cells, dermal sheath cells, or hair follicle dermal cells derived from scalp or face). In some embodiments, the hair follicle dermal cells are derived from frontal, temporal, mid scalp, top of head, vertex, or parietal region of the scalp. In various embodiments, the skin substitutes described above contain epithelial cells and neural crest-derived mesenchymal cells from a human. In some embodiments, the skin substitutes further comprise collagen. In some embodiments, the skin substitutes are combined in therapeutically effective concentrations (e.g., concentrations not naturally found in combination in host tissue) and/or stored in a non-naturally occurring culture medium (e.g., Hanks media, keratinocyte-conditioned medium, or other cell culture media).

In various embodiments, the skin substitutes described above comprise mesenchymal cells (e.g., hair follicle dermal cells) provided within a matrix, e.g., a ground substance matrix or a collagen matrix such as a collagen type I matrix. In various embodiments, the skin substitutes described above are provided in a suspension such as a microsphere.

In various embodiments, the skin substitutes described above comprise keratinocytes that are from one or more of neonatal foreskin keratinocytes, adult keratinocytes, or keratinocyte-like cells derived from pluripotential stem cells or from epithelial cells. In some embodiments, the epithelial cells are primary cells or early passage cells (e.g., first through fourth passage, more preferably first or second passage). In some embodiments, the primary or early passage epithelial cells are mesenchymal cells. In some embodiments, the primary or early passage epithelial cells are hair follicle dermal cells. In some embodiments, the cells are the cells are passaged in keratinocyte-conditioned medium.

In various embodiments, the epithelial cells and mesenchymal cells are autologous. For instance, the epithelial cells and hair follicle dermal cells can be autologous. In some embodiments, the cells are allogenic.

In certain aspects of this invention, the neural-crest derived mesencymal cells, the scalp- or face-derived mesencymal cells, and the hair follicle dermal cells, including dermal papilla cells and dermal sheath cells, are not derived from an occipital or nape region of the scalp. For example, neural-crest derived mesencymal cells, the scalp- or face-derived mesencymal cells, and the hair follicle dermal cells, including dermal papilla cells and dermal sheath cells present in any composition or skin substitute described herein may be isolated from frontal, temporal, mid scalp, top of head, vertex, or parietal region of the scalp or from the face.

Also disclosed herein are methods for transplanting cells capable of inducing human hair follicles, comprising delivering to a human subject any one of the skin substitutes discussed above. In some embodiments, the epithelial cells discussed above are transplanted on their own (e.g., by coating, implanting, and/or injecting the cells into or onto a transplant site in a patient). In some embodiments, the mesenchymal cells discussed above are transplanted on their own (e.g., by coating, implanting, and/or injecting the cells into or onto a transplant site in a patient). In some embodiments, the epithelail cells are transplanted in combination with the mesenchymal cells. In some embodiments, the epithelail cells are transplanted in combination with the mesenchymal cells at therapeutically effective concentrations (e.g., concentrations not naturally found in combination in host tissue). In some embodiments, the transplanted cells can be used to induce hair follicle growth or hair follicle neogenesis.

Also disclosed are methods of treatment comprising transplanting the skin substitutes, as described above. In some embodiments, the subject to be treated with any of the compositions or methods described above has a partial-thickness skin loss, full-thickness skin loss, a wound, a burn, a scar, or hair loss. In some embodiments, transplanting the skin substitute induces eccrine glands and/or sebaceous glands.

In some embodiments, the epithelial cells and/or mesenchymal cells are for use in the methods described above, or are formulated for use in the methods, or are used in the preparation of a medicament for use in the methods described above.

Also disclosed herein are microspheres comprising neural crest-derived mesenchymal cells and/or epithelial cells. In some embodiments, the microspheres comprise both mesenchymal cells (e.g., hair follicle dermal cells) and epithelial cells (e.g., keratinocytes). In some embodiments, the mesenchymal cells are hair follicle dermal cells, such as dermal papilla cells, dermal sheath cells, or hair follicle dermal cells derived from scalp or face). In certain embodiments, the scalp or face-derived hair follicle dermal cells are from a frontal, temporal, mid scalp, top of head, vertex, or parietal region of the scalp, but not derived from an occipital or nape region of the scalp. In some embodiments, the the epithelial cells and neural crest-derived mesenchymal cells in the microspheres are human cells, and may further comprise collagen. For example, in certain embodiments, the microsphere comprises scalp- or face-derived mesenchymal cells (e.g., human cells), wherein the mesenchymal cells are not derived from an occipital or nape region of the scalp.

In some embodiments, the microspheres described above can further comprise a matrix, e.g., a ground substance matrix or a collagen matrix such as a collagen type I matrix to contain the dermal. In some embodiments, the keratinocytes in the microspheres are from one or more of neonatal foreskin keratinocytes, adult keratinocytes, or keratinocyte-like cells derived from pluripotential stem cells or from epithelial cells. In some embodiments, the epithelial cells in microspheres are primary cells or early passage cells (e.g., first through fourth passage, more preferably first or second passage). In some embodiments, the primary or early passage epithelial cells are mesenchymal cells. In some embodiments, the primary or early passage epithelial cells are hair follicle dermal cells. In some embodiments, the cells are the cells are passaged in keratinocyte-conditioned medium.

In various embodiments, the microspheres described above comprise autologous mesenchymal cells and/or epithelial cells. In some embodiments, the mesenchymal cells and/or epithelial cells are allogenic.

In various embodiments, methods are disclosed herein for transplanting cells capable of inducing human hair follicles to a subject, comprising delivering to a human subject any of the microspheres described above. In some embodiments, the microsphere is subdermally or intradermally delivered to a subject. In various embodiments, a method for inducing hair follicle growth or hair follicle neogenesis is provided, comprising delivering to a human subject any of the microspheres described above. In some embodiments, the microsphere is subdermally or intradermally delivered to a subject. In various embodiments, the subject has partial-thickness skin loss, full-thickness skin loss, a wound, a burn, a scar, or hair loss.

In various embodiments, a composition is provided herein for use in inducing hair follicle growth or hair follicle neogenesis in a subject, comprising any of the microspheres described above. Also disclosed herein are the microspheres described above for use in the manufacture of a medicament for inducing hair follicle formation or for inducing hair follicle neogenesis in a subject. In various embodiments, the subject has partial-thickness skin loss, full-thickness skin loss, a wound, a burn, a scar, or hair loss.

Also disclosed herein are methods for making a skin substitute, comprising (a) mixing a culture of primary or early-passage neural crest-derived mesenchymal cells with a matrix; and (b) overlaying a culture of primary or early-passage epithelial cells onto the mixture of (a). For example, the method can comprise (a) mixing a culture of scalp- or face-derived mesenchymal cells with a matrix; and (b) overlaying a culture of primary or early-passage epithelial cells onto the mixture of (a), wherein the mesenchymal cells are not derived from an occipital region of the scalp. As another example, the method can comprise (a) mixing a culture of hair follicle dermal cells with a matrix; and (b) overlaying a culture of primary or early-passage epithelial cells onto the mixture of (a), wherein the hair follicle dermal cells are not derived from an occipital region of the scalp. In various embodiments, the matrix is a collagen matrix (e.g., a collagen type I matrix). In various embodiments, the cells are cultured in keratinocyte-conditioned medium.

In certain embodiments, the compositions described and exemplified herein induce hair follicle formation when provided to human subjects, wherein the hair follicle that is formed is fully human and therefore does not elicit a host immune response.

BRIEF DESCRIPTION OF THE DRAWINGS

The accompanying drawings, which are incorporated in and constitute a part of this specification, illustrate several non-limiting embodiments of the invention and together with the description, serve to explain the principles of the invention.

FIG. 5A shows positive signal in fluorescent in situ hybridization analysis using a human-specific pan-centromeric probe (green) shows that both the hair follicle and dermal papilla are derived from human cells. FIG. 5B uses a human Y chromosome-specific probe (red) to mark the hair follicle. The probe bound to foreskin keratinocytes (male origin), and not the dermal papilla cells (female origin), indicating that the newly formed dermal papilla was of female origin.

FIGS. 6A, 6B, and 6C show that grafts formed by a skin substitute comprising human neonatal foreskin keratinocytes, human dermal papilla cells, and type I collagen stain positively for markers of fully developed hair follicles. FIG. 6A: alkaline phosphatase activity (blue stain) is observed in the dermal papilla and lower dermal sheath. FIG. 6B: a human-specific Nestin antibody stains cells in the dermal papilla and lower dermal sheath. FIG. 6C: a human-specific Versican antibody stains mesenchymal cells in the dermal sheath region.

FIGS. 8A and 8B show that hair follicles in grafts formed by a skin substitute comprising human neonatal foreskin keratinocytes, human dermal papilla cells, and type I collagen display normal expression of Keratin 15 and Keratin 75.

FIG. 8A: Keratin 15 is immunoreactive in the basal layer of the outer root sheath. FIG. 8B: Keratin 75 is immunoreactive in the hair follicle companion layer.

FIG. 11 shows the tabulated results of the experiment shown in FIG. 10. The optimal passage of human keratinocytes for hair follicle regeneration is the early passage keratinocytes. The early passage grafts had more and larger hair follicles with widest hair shafts. * Significantly less than primary keratinocytes, p<0.05, ** Significantly greater than passaged keratinocytes, p<0.02

FIGS. 16A, 16B, and 16C show H&E and toluidine blue staining in dermal-epidermal composite grafts after 15 weeks. FIGS. 16A-C show telogen hair follicles, confirmed by club-like appearance and spiky keratin fibers (FIG. 16A), secondary hair germ with adjacent hair papilla (FIG. 16B), and presence of a cornified club (FIG. 16C, toluidine blue staining).

FIGS. 17A and 17B show Ki-67 staining of dermal-epidermal composite grafts. FIG. 17A shows that telogen hair follicles do not contain Ki-67-positive cells, consistent with the telogen stage of the hair follicle (arrow). FIG. 17B shows an anagen hair follicle with dermal papilla (arrow), including dense Ki-67 reactivity.

FIG. 18A shows a representative H&E stained section of a dermal-epidermal composite graft, showing hair follicle inner and outer root sheath, and sebaceous gland. FIG. 18B is antibody staining for cathelicidin in the dermal-epidermal composite graft, showing that sebaceous gland was highly immunoreactive to an antibody for cathelicidin, an antimicrobial peptide.

DETAILED DESCRIPTION OF EXEMPLARY EMBODIMENTS

Figure 1:
FIG. 1 shows pilosebaceous units, including hair follicles, formed by grafting a skin substitute comprising human neonatal foreskin keratinocytes, human dermal papilla cells, and type I collagen. Sections were obtained 8 weeks after grafting onto nude mice.

The invention provides skin substitutes comprising epithelial cells and neural crest-derived mesenchymal cells. In one embodiment, the mesenchymal cells are hair follicle dermal cells, which include, for example, dermal papilla cells and dermal sheath cells. The neural crest-derived mesenchymal cells may be derived from scalp or face. In one embodiment, the neural crest-derived mesenchymal cells are derived from a frontal, temporal, mid scalp, top of head, vertex, or parietal region of the scalp. In some aspects, the neural crest-derived mesenchymal cells are not derived from an occipital or nape region of the scalp. In some aspects, the epithelial cells and neural crest-derived mesenchymal cells are human. In some aspects, the epithelial cells are keratinocytes or keratinocyte-like cells. The skin substitute may further comprise collagen.

A skin substitute comprising epithelial cells and scalp- or face-derived mesenchymal cells, wherein the mesenchymal cells are not derived from an occipital or nape region of the scalp is also encompassed. In this embodiment, the mesenchymal cells may be hair follicle dermal cells. The hair follicle dermal cells may be dermal papilla cells or dermal sheath cells. In some aspects that epithelial cells may be keratinocytes or keratinocyte-like cells. In some aspects the dermal papilla cells are derived from frontal, temporal, mid scalp, top of head, vertex, or parietal region of the scalp. In some aspects the scalp- or face-derived mesencymal cells and the epithelial cells are human. The skin substitute may further comprise collagen.

In another embodiment, a skin substitute comprising epithelial cells and hair follicle dermal cells, wherein the dermal cells are not derived from an occipital or nape region of the scalp is encompassed. In some embodiments the epithelial cells are keratinocytes or keratinocyte-like cells. In some embodiments, the hair follicle dermal cells are dermal papilla cells or dermal sheath cells. In some aspects the cells of the skin substitute are human. In some aspects the hair follicle dermal cells are derived from a frontal, temporal, mid scalp, top of head, vertex, or parietal region of the scalp. The skin substitute may further comprise collagen.

In some embodiments, the skin substitutes described herein are provided with a matrix. The matrix may be a collagen matrix or a ground substance matrix. In some embodiments, the matrix is a type I collagen matrix.

In certain embodiments, the epithelial cells of the skin substitute comprise keratinocytes. In some aspects the keratinocytes are neonatal foreskin keratinocytes (NFK).

The skin substitutes comprising epithelial cells may comprise primary cells or early-passage epithelial cells, wherein early-passage cells are from a first, second, or third passage. In some aspects, the epithelial cells are keratinocytes and the keratinocytes are primary cells or early-passage keratinocyte cells, wherein early-passage cells are from a first, second, or third passage.

The skin substitute comprising mesencymal cells may comprise primary cells or early-passage cells, wherein early-passage cells are from a first, second, third, or fourth passage. In some embodiments, the skin substitute comprises primary or early-passage dermal papilla cells, wherein early-passage dermal papilla cells are from a first, second, third, or fourth passage.

The epithelial cells and mesenchymal cells may be derived from a same or different donor. The keratinocytes and dermal papilla cells may be derived from a same or different donor. In some aspects, the cells of the skin substitute are passaged in keratinocyte-conditioned medium. In some embodiments, the epithelial cells and mesenchymal cells are autologous. In some embodiments, the epithelial cells and hair follicle dermal cells are autologous. In some aspects the epithelial cells and mesenchymal cells are allogenic. In some aspects the epithelial cells and hair follicle dermal cells are allogenic.

Methods for transplanting cells capable of inducing human hair follicles are encompassed, comprising delivering to a human subject or patient a skin substitute described herein, such as the skin substitute of any of the claims.

Methods for inducing hair follicle growth or hair follicle neogenesis comprising delivering to a human subject the skin substitute of any one of the claims are also encompassed.

Compositions for use in inducing hair follicle growth or hair follicle neogenesis comprising the skin substitute of any one of the claims are fully encompassed.

Uses of a skin substitute of any one of the claims in the manufacture of a medicament for inducing hair follicle formation or for inducing hair follicle neogenesis are encompassed.

In some embodiments, a subject in need of inducing hair follicle growth has partial-thickness skin loss, full-thickness skin loss, a wound, a burn, a scar, or hair loss.

In some embodiments, the skin substitute of the invention induces eccrine glands. In some embodiments, the skin substitute of the invention induces sebaceous glands.

Methods for transplanting cells capable of inducing hair follicles, comprising subdermally or intradermally delivering to a human subject neural crest-derived mesenchymal cells are provided. In some embodiments, the methods further comprise transplanting epithelial cells sequentially or simultaneously with the mesenchymal cells, optionally with collagen.

Methods for transplanting cells capable of inducing hair follicles, comprising subdermally or intradermally delivering to a human subject scalp-derived mesenchymal cells, wherein the mesenchymal cells are not derived from an occipital region of the scalp together with epithelial cells and optionally collagen are encompassed.

Methods for transplanting cells capable of inducing hair follicles, comprising subdermally or intradermally delivering to a patient hair follicle dermal cells, such as, dermal papilla cells or dermal sheath cells, wherein the hair follicle dermal cells are not derived from an occipital or nape region of the scalp are also encompassed.

Methods of making skin substitutes, comprising (a) mixing a culture of primary or early-passage neural crest-derived mesenchymal cells with a matrix; and (b) overlaying a culture of primary or early-passage epithelial cells onto the mixture of (a) are encompassed, as are methods of making skin substitutes, comprising (a) mixing a culture of scalp-derived mesenchymal cells with a matrix; and (b) overlaying a culture of primary or early-passage epithelial cells onto the mixture of (a), wherein the mesenchymal cells are not derived from an occipital region of the scalp. In some embodiments, methods of making skin substitutes, comprising (a) mixing a culture of hair follicle dermal cells, such as dermal papilla cells or dermal sheath cells, with a matrix; and (b) overlaying a culture of primary or early-passage epithelial cells onto the mixture of (a), wherein the dermal papilla cells are not derived from an occipital region of the scalp are encompassed.

In some embodiments, compositions comprising human dermal papilla cells for inducing hair follicle neogenesis are encompassed. In one aspect the human dermal papilla cells are isolated from the frontal, temporal, or parietal region of human scalp. In one aspect the human dermal papilla cells are not isolated from the occipital or nape region of human scalp. The composition may comprise human dermal papilla cells and human keratinocytes. The composition may comprise human dermal papilla cells, human keratinocytes, and collagen.

The invention provides a method for inducing human hair follicle growth in humans. In one aspect the method comprises delivering to a human subject a composition comprising human dermal papilla cells and human keratinocytes, optionally in combination with collagen. In some aspects the composition is delivered subdermally or intradermally.

In one embodiment, the method comprises delivering to a human subject a composition comprising human dermal papilla cells that are derived from the frontal, temporal, or parietal region of the human scalp together with human keratinocytes, optionally in combination with collagen. In some aspects the composition is delivered subdermally or intradermally.

The invention also provides uses for a composition comprising human dermal papilla cells and human keratinocytes, optionally in combination with collagen, in the manufacture of a medicament for inducing hair follicle formation or for inducing hair follicle neogenesis. In some aspects the composition is delivered subdermally or intradermally.

The invention also provides a pharmaceutical composition comprising human dermal papilla cells and human keratinocytes, optionally in combination with collagen, for use in treating a subject who is at risk for, diagnosed with, or who has hair loss or is in need of hair follicle neogenesis.

In yet another embodiment, methods and uses comprising grafting to a human subject a composition or skin substitute of the invention are encompassed. In some aspect the human subject is in need of hair growth.

In one embodiment, the method and use comprises delivering to a human subject a composition or skin substitute of the invention, wherein the subject has partial-thickness skin loss, full-thickness skin loss, a wound, a burn, a scar, or hair loss. In another embodiment, the method and use induces formation of eccrine glands. In yet another embodiment, the method and use induces formation of sebaceous glands.

In one embodiment, the neural crest-derived mesenchymal cells or hair follicle dermal cells, such as, for example, dermal papilla cells, are incorporated into a microsphere. In another embodiment, the microsphere further comprises epithelial cells. In another embodiment, the microspheres are formed by mixing human dermal papilla cells and keratinocytes (e.g., neonatal foreskin keratinocytes) in a 1:1 mixture of dermal papilla medium and keratinocyte serum free medium, and incubating the clusters for about four weeks. In another embodiment, the neural crest-derived mesenchymal cells or hair follicle dermal cells are provided with a matrix. In yet another embodiment, the matrix is a collagen matrix or a ground substance matrix. In yet another embodiment, the matrix is a type I collagen matrix. In yet another embodiment, the matrix is a rat type I collagen matrix, a bovine type I collagen matrix, or a human type I collagen matrix.

In one embodiment, the epithelial cells comprise one or more epithelial cells from different sources. In another embodiment, the epithelial cells are keratinocytes or keratinocyte-like cells. In yet another embodiment, the keratinocytes are neonatal foreskin keratinocytes (NFKs). In another embodiment, the keratinocytes or keratinocyte-like cells are induced pluripotent stem (iPS) cells differentiated into keratinocytes.

In one embodiment, the mesenchymal cells and/or epithelial cells are derived from the same donor. In another embodiment, the donor is the patient. In yet another embodiment, the mesenchymal cells and/or epithelial cells are derived from different donors. In yet another embodiment, the donor of either the mesenchymal or epithelial cells is the patient.

1. Definitions

As used herein, the singular forms "a" "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

As used herein, the terms "about" and "approximately" mean within an acceptable error range for the particular value as determined by one of ordinary skill in the art, which will depend in part on how the value is measured or determined, i.e., the limitations of the measurement system. For example, "about" can mean from 1 to 1.5 standard deviation(s) or from 1 to 2 standard deviations, per the practice in the art. Alternatively, "about" can mean a range of up to and including 20%, 10%, 5%, or 1% of a given value. Alternatively, particularly with respect to biological systems or processes, the term can mean up to and including an order of magnitude, up to and including 5-fold, and up to and including 2-fold, of a value. Where particular values are described in the application and claims, unless otherwise stated the term "about" meaning within an acceptable error range for the particular value should be assumed.

As used herein, the term "apocrine gland" refers to glands in the skin that have a coiled, tubular excretory portion with widely dilated lumen, lined by cuboidal epithelial cells with eosinophilic cytoplasm and apical snouts, and an outer discontinuous layer of myoepithelial cells resting on a prominent basement membrane.

As used herein, the term "composition" refers to a mixture that contains a therapeutically active component(s) and a carrier, such as a pharmaceutically acceptable carrier or excipient that is conventional in the art and which is suitable for administration to a subject for therapeutic purposes. The therapeutically active component may include the mesenchymal cells of the invention. In other embodiments, term "composition" refers to the skin substitutes of the invention, which are described in further detail below. The compositions of the invention may further comprise a matrix, which is defined below.

As used herein, the term "dermal papilla" refers to the follicular dermal papilla, i.e., the mesenchymal cell condensation at the base of the hair follicle.

As used herein, the term "dermal sheath" refers to the region of connective tissue that envelops the hair follicle.

As used herein, the term "eccrine glands" refers to sweat glands in the skin. Eccrine glands consist of two anatomical portions: (1) the secretory coil, located in the deep dermis at the junction with the subcutaneous tissue and composed of clear pyramidal cells and dark-stained cells, surrounded by a single outer discontinuous layer of myoepithelial cells resting on a well-defined basement membrane; and (2) the excretory part composed of a straight intradermal portion and an intraepidermal spiral portion (acrosyringium), and a double layer of small cuboidal cells with no underlying myoepithelial layer.

As used herein, the term "endothelial cell" refers to the specialized cells that line the inner walls of blood vessels.

As used herein, the term "epidermal cell" refers to cells derived from the epidermis of the skin. Epidermal cells are one type of epithelial cells. Examples of epidermal cells include, but are not limited to keratinocytes, melanocytes, Langerhans cells, and Merkel cells.

As used herein, the term "epithelial cell" refers to cells that line the outside (skin), mucous membranes, and the inside cavities and lumina of the body. In particular embodiments, the term "epithelial cell" refers to stratified squamous epithelial cells. Most epithelial cells exhibit an apical-basal polarization of cellular components. Epithelial cells are typically classified by shape and by their specialization. For example, squamous epithelial cells are thin and have an irregular flattened shape mainly defined by the nucleus. Squamous cells typically line surfaces of body cavities, such as the esophagus. Specialized squamous epithelia line blood vessels (endothelial cells) and the heart (mesothelial cells). Cuboidal epithelial cells are cube-shaped and usually have their nucleus in the center. Cuboidal epithelial cells are typically found in secretive or absorptive tissue, e.g., kidney tubules, glandular ducts, and the pancreatic exocrine gland. Columnar epithelial cells are longer than they are wide and the elongated nucleus is usually near the base of the cell. These cells also have tiny projections, called microvilli, which increase the surface area of the cells. Columnar epithelial cells typically form the lining of the stomach and intestines, as well as sensory organs.

As used herein, the term "hair follicle" or "HF" refers to a tubular infolding of the epidermis from which a hair may grow. A hair follicle may contain a hair shaft in the correct anatomical location, exhibit long-term graft survival, normal hair follicle cycling, and sebaceous glands.

As used herein, the term "hair follicle dermal cell" refers to mesenchymal cells in the dermis, including dermal papilla cells and dermal sheath cells.

As used herein, the term "hair regeneration" refers to the stimulation of existing quiescent hair follicles to enter the anagen phase of hair growth. The term also refers to stimulation of hair formation from hair follicle remnants or components of hair follicles (e.g., implantation of microdissected dermal papilla with or without follicular epithelium, or hair growth after plucking), rather than starting with intact quiescent hair follicles.

As used herein, the term "hair neogenesis" refers to the stimulation of de novo hair follicle growth where no hair follicle previously existed in skin with no preexisting hair follicles, or in skin with fewer than the desired number of hair follicles.

As used herein, the term "keratinocyte" refers to epithelial cells in the epidermis of the skin (including cells in the follicular epithelium) that undergo cell division and stratification from basal cells in contact with the epidermal basement membrane into squamous cells. Keratinocytes express keratin. In some embodiments, keratinocytes can be derived from iPS cells.

As used herein, the term "keratinocyte-like cell" refers to cells that express keratin and have the ability to form a stratified squamous epithelium or follicular epithelium. Keratinocyte-like cells may be derived from skin cells or other organs such as bone marrow or trachea, or from cells with stem-cell features (including embryonic stem cells) or that induce pluripotent stem cells. In some embodiments, keratinocyte-like cells can be derived from iPS cells.

As used herein, the terms "matrix" and "ground substance" refer to any natural or synthetic extracellular matrix-like composition capable of forming a hydrated gel-like cellular support. Cells may be deposited within or on matrices and ground substances. Matrices and ground substances may comprise one or more fibrous proteins having both structural and adhesive functions. Such proteins include, but are not limited to elastin, fibronectin, laminin, and collagens I, II, III, IV, V, VI, VII, VIII, IX X, XI, and XII. Alternatively, or in addition, matrices and ground substances may comprise proteoglycan molecules comprising polysaccharide chains covalently linked to proteins. Such proteoglycans include, but are not limited to, hyaluronan-, heparin sulfate-, chondroitin-, keratin sulfate-, and dermatin sulfate-linked proteins.

As used herein, the term "mesenchymal cell" refers to multipotent cells with the capacity or potential capacity to induce hair follicle formation similar to cells of the dermal papilla and connective tissue sheath from hair follicles. Mesenchymal cells are usually considered mesodermal connective tissue cells that express vimentin, but cells with the desired attributes may also be neural crest derived. Mesenchymal cells may be isolated from one or more of the following sources: patient skin or mucosa for autologous cells; donor skin or mucosa for allogeneic cells; normal skin or mucosa; skin with an adnexal tumor; and other tissues (e.g. fat, bone marrow). Mesenchymal cells include, but are not limited to, fibroblasts, dermal papilla cells, dermal sheath cells, onychofibroblasts (fibroblasts from nail unit), dental pulp cells, periodontal ligament cells, neural crest cells, adnexal tumor cells, induced pluripotent stem cells, and mesenchymal stem cells from bone marrow, umbilical cord blood, umbilical cord, fat, and other organs.

As used herein, the terms "morphologically correct" and "fully developed" refers to hair follicles that have a normal configuration with an epithelial filament coming out of the distal end of the follicle and dermal papilla sitting at the base of the follicle. The follicles also have cells proliferating at the base of the follicle, and have concentric layers of outer and inner root sheath, cuticle and cortex. The follicles exhibit normal differentiation of the outer root sheath, and have hair shafts and sebaceous glands. The hairs go through normal cycles, and contain an epithelial stem cell component.

As used herein, the term "pharmaceutically acceptable carrier" refers to a non-toxic solid, semisolid, or liquid filler, diluents, encapsulating material, formulation auxiliary, or excipient of any conventional type. A pharmaceutically acceptable carrier is non-toxic to recipients at the dosages and concentrations employed, and is compatible with other ingredients of the formulation.

As used herein, the term "neural crest-derived mesenchymal cells" refers to cells having origins in the neural crest (i.e., a transient embryonic structure in vertebrates) that have the capacity to self-renew and display developmental potential. Neural crest cells originate in the ectoderm at the margins of the neural tube and, after a phase of epithelial-mesenchymal transition and extensive migration, settle down in different parts of the body to contribute to the formation of a variety of different tissues and organs. See Shakhova, "Neural crest-derived stem cells," http://www.st-embook.org/node/696 (incorporated herein by reference). Neural crest derivatives originate from four major segments of the neuraxis: cranial, cardiac, vagal, and trunk neural crest. Id. Neural crest cells from the trunk are able to produce mesenchymal derivatives. Id.

As used herein, the term "primary cells" refer to cells harvested and cultured directly from a donor source without further passage.

As used herein, the term "early-passage cells" refer to cells harvested and cultured from a donor and passaged fewer than three times (in the case of epithelial cells), or fewer than five times (in the case of mesenchymal or hair follicle dermal cells).

As used herein, the term "sebaceous gland" refers to hair follicle-dependent glands that originate as a budding of sebaceous glands primordium. Sebaceous glands consist of multiple lobules of rounded cells (sebocytes), filled with lipid-containing vacuoles, and rimmed by a single layer of small, dark germinative cells. The lobules converge on a short duct, which empties the lipid content of degenerated sebocytes into the hair follicle.

As used herein, the terms "skin substitute," "skin equivalent," "dermal-epidermal composite," and "skin graft" refer to any product used for the purpose of damaged skin replacement, fully or partially, temporarily or permanently, and possessing some similarities with human skin, both anatomically or functionally. Skin substitutes include, but are not limited to, bioengineered skin equivalents, tissue-engineered skin, tissue-engineered skin constructs, biological skin substitutes, bioengineered skin substitutes, skin substitute bioconstructs, living skin replacements, dermal-epidermal composites and bioengineered alternative tissue.

As used herein, the term "microsphere" includes but is not limited to cell clusters and cell aggregates optionally comprising a biodegradable microsphere.

As used herein, the term "treatment," refers to any administration or application of remedies for a condition in a mammal, including a human, to obtain a desired pharmacological and/or physiological effect. Treatments include inhibiting the condition, arresting its development, or relieving the condition, for example, by restoring or repairing a lost, missing, or defective function, or stimulating an inefficient process, or improving symptoms of the condition.

As used herein, the term "trichogenic" refers to the ability of a cell to induce a hair follicle and/or to promote hair follicle morphogenesis, i.e., folliculogenesis.

2. Skin Substitutes and Microspheres of the Invention

It has been surprisingly found that neural crest-derived mesenchymal cells are trichogenic. Specifically, mesenchymal cells derived from a region of the face or scalp other than the occipital or nape regions are capable of inducing hair follicles. Such follicles are complete according to the criteria proposed by Chuong et al., "Defining hair follicles in the age of stem cell bioengineering," *J. Invest. Dermatol.*, 127:2098-100 (2007). The follicles have a normal configuration with an epithelial filament coming out of the distal end of the follicle and dermal papilla sitting at the base of the follicle. The follicles have cells proliferating at the base of the follicle, and have concentric layers of outer and inner root sheath, cuticle and cortex. The follicles exhibit normal differentiation of the outer root sheath, and have hair shafts and sebaceous glands. The hairs go through normal cycles, and contain an epithelial stem cell component.

Accordingly, the invention provides cellular compositions capable of hair neogenesis. In one embodiment, the invention provides a skin substitute comprising epithelial cells and trichogenic cells. Another embodiment of the invention provides microspheres comprising trichogenic cells.

In one embodiment, the trichogenic cells are derived from the neural crest. In another embodiment, the trichogenic cells are isolated from the scalp or face. In another embodiment, the trichogenic cells are not derived from an occipital or nape region of the scalp. In another embodiment, the trichogenic cells are hair follicle dermal cells.

a) General Characteristics of Mammalian Skin

Mammalian skin contains two primary layers: an outer layer called the epidermis and an inner layer called the dermis. The epidermis primarily contains keratinocytes that are formed in the deeper layers of the epidermis by mitosis and then migrate up to the surface, where they are eventually shed. The dermis contains a variety of structures including hair follicles, sebaceous glands, sweat glands, apocrine glands, nerves, lymphatic vessels, and blood vessels.

Hair follicle morphogenesis takes place mostly in utero during embryogenesis. Hair follicle formation begins with the appearance of epidermal placodes, which mark the location of the new hair follicle. Mesenchymal cells (i.e., inductive multipotent cells) then begin to aggregate in the dermis below the epidermal placodes. The mesenchymal aggregates signal to the keratinocytes in the overlaying placodes, which then begin growing downward into the dermis. When the epidermal keratinocytes reach the mesenchymal aggregates, the cells undergo a series of differentiation and proliferation processes, eventually forming a mature hair follicle.

Mature hair follicles contain four main parts: the dermal papilla (DP), dermal sheath (DS), follicular epithelium, and hair shaft (FIG. 1D). The DP is located at the base, or bulb, of the hair follicle adjacent to the hair matrix that produces the hair shaft. The DS is made up of connective tissue and envelops the hair follicle. The follicular epithelium includes the outer root sheath and the inner root sheath. The hair shaft is a proteinaceous structure that extends from the base of the follicle through the epidermis to the exterior of the skin.

The hair follicle is a dynamic miniorgan that repeatedly cycles through periods of growth (anagen), regression (catagen), and quiescence (telogen). The lower portion of the hair follicle regresses or regrows, regenerating in each cycle through complicated interactions between the dermal mesenchymal cells and epidermal cells. The permanent portion of the lower hair follicle above the continuously remodeled part is referred to as the "bulge" because it protrudes slightly from the follicle. The bulge contains multipotent cells capable of forming the follicle, sebaceous gland, and epidermis. As individuals age, the anagen and catagen phases of the hair follicle cycle become shorter, and hair follicles experience a more rapid shift to the telogen phase. As a result, normal hairs are gradually replaced by finer vellus hairs, and in some individuals, the cells may lose their trichogenic properties entirely.

b) Skin Cells for Use in the Invention

The skin substitutes of the invention may comprise either (1) mesenchymal cells, or (2) mesenchymal cells and epithelial cells. In the embodiments wherein the skin substitutes comprise mesenchymal cells and no epithelial cells, the mesenchymal cells interact with the patient's epithelial cells to produce a hair follicle. In the embodiments wherein the skin substitute comprises mesenchymal cells and epithelial cells, the mesenchymal and epithelial cells supplied in the skin substitute interact, with or without the patient's epithelial cells, to produce a hair follicle.

(1) Mesenchymal Cells

Mesenchymal cells are usually considered mesodermal connective tissue cells that express vimentin, but vimentin-expressing cells with these attributes may also be neural crest derived. Sources of cells include the inductive multipotent cells of the dermal papilla and connective tissue sheath from hair follicles. It has been surprisingly found that mesenchymal cells (i.e., inductive multipotent cells) isolated from certain sources are trichogenic. For example, the inventors have found that neural crest-derived mesenchymal cells are trichogenic. The inventors have also found that mesenchymal cells, such as hair follicle dermal cells, harvested from the face or scalp at regions other than the occipital region or nape region, are trichogenic.

(2) Epithelial Cells

Generally, any source of epithelial cells or cell line that can stratify into squamous epithelia are useful in the present invention. Accordingly, the present invention is not limited to the use of any particular source of cells that are capable of differentiating into squamous epithelia. Indeed, the present invention contemplates the use of a variety of cell lines and sources that can differentiate into stratified squamous epithelia. Sources of cells include primary and immortalized keratinocytes, keratinocyte-like cells, and cells with the capacity to be differentiated into keratinocyte-like cells, obtained from humans and cavaderic donors (Auger et al., In Vitro Cell. Dev. Biol. Animal 36:96-103; and U.S. Pat. Nos. 5,968,546 and 5,693,332), neonatal foreskin (Asbill et al., Pharm. Research 17(9):1092-97 (2000); Meana et al., Burns 24:621-30 (1998); and U.S. Pat. Nos. 4,485,096; 6,039,760; and 5,536,656), and immortalized keratinocytes cell lines such as NM1 cells (Baden, In Vitro Cell. Dev. Biol. 23(3): 205-213 (1987)), HaCaT cells (Boucamp et al., J. cell. Boil. 106:761-771 (1988)); and NIKS cells (Cell line BC-1-Ep/SL, U.S. Pat. No. 5,989,837; ATCC CRL-12191).

Epithelial cells may also be obtained from: patient skin or mucosa (autologous), donor skin or mucosa (allogeneic), epidermal cell lines, epidermal cells derived from stem cells, primary or passaged epidermal cells, trachea, and cells derived from blood mononuclear cells or circulating stem cells. Subpopulations of epithelial cells from these sources may also be used, for example by enriching the number of cells with stem-cell properties. Epithelial cells express keratin or can be induced to express keratin, and have the capacity of forming a stratified squamous epithelium and/or follicular epithelium.

In some embodiments, the epithelial cells are from two different sources. For example, the invention may be practiced using immortalized keratinocytes together with autologous keratinocytes. The relative proportion of autologous cells to immortalized cells may be 1:99, 5:95, 10:90, 20:80, 30:70, 40:60, 50:50, 60:40, 70:30, 80:20, or 90:10. In this way, the number of autologous keratinocytes may be reduced. The immortalized keratinocytes may be enhanced to promote skin healing, for example by genetically modifying the cells to express growth factors or angiogenic factors. The immortalized keratinocytes may be modified so that they can be targeted for elimination at any point following engraftment. Specifically, in one embodiment, so called "suicide genes" may be used and the cells can be genetically modified so that they die in response to a drug treatment. (See Vogler et al., An Improved Bicistronic CD20/tCD34 Vector for Efficient Purification and In Vivo Depletion of Gene-Modified T Cells for Adoptive Immunotherapy., Mol Ther. doi:10.1038 (May 11, 2010) (advanced online epublication); and Scaife et al., Novel Application of Lentiviral Vectors Towards Treatment of Graft-Versus-Host Disease, Expert Opin Biol Ther. 2009 June; 9(6):749-61.)

(3) Isolating Cells

Mesenchymal and epithelial cells may be isolated using any suitable techniques. For example, mesenchymal cells may be isolated by migration of cells from tissue explants. Alternatively, cells may be dissociated from skin or mucosa samples or skin tumors to isolate mesenchymal and epithelial cells. In addition, epithelial cells may be isolated by inducing multipotent stem cells to differentiate into epithelial cells. Exemplary methods for isolating cells are described in the Examples.

Isolated cells may be grown in any suitable medium known to those skilled in the art. Exemplary media are discussed in the Examples. The samples may be enriched for hair inductive cells based on any technique known to those skilled in the art. For example, cells may be selected based on the presence of suitable cell markers, such as CD133, CD10, or nestin. Alternatively, growth factors such as BMP2, 4, 5, or 6, Wnt-3a, Wnt-10b, insulin, FGF2, KGF, etc. may be added to maintain and enrich the hair inductive cells, including dermal papilla cells. Cells may also be enriched for their ability to differentiate into hair follicles using the cell adhesion and cell sorting methods.

3. Exemplary Methods of Making Skin Substitutes and Microspheres of the Invention The invention relates to skin substitutes and microsphere preparations for injection.

a) Skin Substitutes

The skin substitutes of the invention contain different cell types than prior art skin substitutes, yet may be prepared by using similar methods to those known in the art. For example, Greenberg S et al., "In vivo transplantation of engineered human skin," Methods Mol Biol., 289:425-30 (2005) discloses methods for creating in vitro skin substitutes. In addition, Shevchenko R V et al., "A review of tissue-engineered skin bioconstructs available for skin reconstruction," J R Soc Interface, 7(43):229-58 (2010) provides a review of various approaches that may be used for preparing skin substitutes. Exemplary methods are also provided in the Examples.

In one embodiment, the compositions comprising the trichogenic cells described herein are provided in the form of a skin substitute. In some embodiments, the skin substitutes are formed by combining the trichogenic cells (or trichogenic cells with fibroblasts, endothelial cells, and/or other supportive mesenchymal cells) with a ground substance or matrix, and then overlaying the construct with epithelial cells. Prior to grafting, the epithelial cells may be induced to partially or fully form a stratified squamous epithelium and cornified layer by exposing the surface of the substitute to air.

In another embodiment, the trichogenic cells may be cultured before combining with a matrix. In another embodiment, the cell-matrix mixture is cultured before combining with the epithelial cells. In another embodiment, the trichogenic cells are grown on or below, rather than being incorporated into, the ground substance or matrix, and this is overlaid with epithelial cells.

In another embodiment, the trichogenic cells are first made into microspheres before being incorporated or inserted into, or laid on, the ground substance/matrix/scaffold, and this is overlaid with epithelial cells. The microspheres may be composed of trichogenic cells with or without epithelial cells and with or without matrix. If the microsphere has a matrix, it may be the same or different in composition from that of dermal scaffold. The ground substance/matrix/scaffold into which the microspheres are placed may be with or without added fibroblasts, endothelial cells, and/or other supportive mesenchymal cells. The spacing of the microspheres may be random or at intervals replicating the spacing of hair follicles in normal human skin.

In another embodiment, the trichogenic cells (or trichogenic cells with fibroblasts or other supportive mesenchymal cells) are used in a dermal construct that is made separately from the epidermal construct, and the two are grafted sequentially to the patient. As an alternative to using an epidermal construct, the epithelial cells may be sprayed onto the grafted dermal construct, using an aerosol of cells in media or in fibrin glue.

Compounds that may be used for the ground substance/matrix/scaffold include collagens, elastin, laminin, fibrin, hyaluronan or hyaluronic acid, fibronectin, chitosan, cellulose, silk fibroin, and alginates. These compounds may be human, rat, porcine, or bovine; from crustaceons or fungi (chitosan) or plants or algae (cellulose); or proteins expressed as recombinant forms in bacteria or other organisms. These compounds may also be modified or combined, such as hair keratin-collagen sponge, hyaluronan coupled with fibronectin functional domains, poly(lactic-co-glycolic acid)/chitosan hybrid nanofibrous membrane, polycaprolactone (PCL) collagen nanofibrous membrane, silk fibroin and alginate, polyvinyl alcohol/chitosan/fibroin blended sponge, tegaderm-nanofibre construct, bacterial cellulose, ICX-SKN skin graft replacement (InterCytex, Cambridge, England), collagen-glycosaminoglycan-chitosan, composite nano-titanium oxide-chitosan, Collatamp® (EUSAPharma, Langhorne, Pa.), deacetylated chitin or plant cellulose transfer membranes. The scaffold may also be human, porcine, or bovine acellular dermis, tendon, or submucosa, that can be lyophilized, cross-linked, meshed, or combined with any of the above compounds. It may be complex mixtures such as Matrigel™ (BD Biosciences) or extracellular matrix derived from fibroblasts or other cells. The matrix, ground substance, or scaffold may also consist of or incorporate synthetic materials, including silicone, polysiloxane, polyglycolic acid, polylactic acid, nylon, PolyActive™ matrix (OctoPlus, Cambridge, Mass.) (polyethylene oxide terephthalate and polybutylene terephthalate), and biodegradable polyurethane microfibers The skin substitute may be supplied sealed in a heavy gauge polyethylene bag with a 10% $CO_2$/air atmosphere and agarose nutrient medium, ready for single use. The skin substitute may be kept in the sealed bag at 68° F.-73° F. (20° C.-23° C.) until use. The skin substitute may be supplied as a circular disk, for example, approximately 75 mm in diameter and 0.75 mm thick. The agarose shipping medium may contain agarose, L-glutamine, hydrocortisone, human recombinant insulin, ethanolamine, O-phosphorylethanolamine, adenine, selenious acid, DMEM powder, HAM's F-12 powder, sodium bicarbonate, calcium chloride, and water for injection. The skin substitute may optionally be stored on a plastic tray or in a cell culture dish within the bag. The skin substitute may be packaged with an epidermal (dull, matte finish) layer facing up and a dermal (glossy) layer facing down, resting on a polycarbonate membrane.

b) Microsphere Preparations for Injection or Implantation

The invention includes microsphere preparations for injection or implantation. These preparations may be prepared by any methods known to those in the art. Exemplary methods are provided in the Examples. In one embodiment, the trichogenic cells are presented in a buffer suitable for injection, such as a sterile saline solution, phosphate buffered saline, Dulbecco's modified Eagle's medium (DMEM), Hank's balanced salt solution, Plasmalyte A, or RPMI. In one embodiment, the trichogenic cells are provided with a matrix or ground substance. The matrix may be natural polymers such as methylcellulose, collagen, chitosan, hyaluronic acid, gelatin, alginate, fibrin, fibronectin, or agarose. The matrix may be complex mixtures such as Matrigel™ or synthetic polymers. In another embodiment, the trichogenic cells are combined with epithelial cells with or without matrix or ground substance before injection or implantation.

In one embodiment, the compositions comprising the trichogenic cells described herein may be subdermally or intradermally injected or implanted at a site where hair growth is desired without further culture. Cells prepared by dissociation methods may be resuspended in buffer and injected directly or first combined with biodegradable microspheres prior to injection or implantation. The cells in culture medium can be stored on ice for 24 or more hours or frozen in liquid nitrogen for long-term storage. For cryopreservation, cells are placed in a solution of 10% DMSO, 70% DMEM and 20% fetal bovine serum. Cells are placed in cryovials at a concentration of 0.1-10 million cells per ml and frozen in a control-rate freezer and stored at −180° C. until the day of injection or implantation. Viability of all thawed cells may be verified to be more than 85% before use.

Compositions comprising trichogenic cells may be injected or implanted into recipient skin or wound. Compositions may also be injected or implanted into grafts (split-thickness grafts or skin substitutes including dermal-epidermal composites and dermal constructs combined with epidermal constructs or cell spraying) before application to the patient or following grafting. In another embodiment, the compositions comprising trichogenic cells may be cultured before injection or implantation.

4. Methods of Administering the Skin Substitutes and Microspheres of the Invention The invention provides methods for transplanting cells to a patient that are capable of inducing human hair follicles in the patient. For example, the skin substitutes of the invention may be grafted onto a patient, and the microspheres of the invention may be injected into a patient.

a) Patients Benefitting from Treatment with the Invention

The skin substitutes and microspheres of the invention are useful for treating patients with full-thickness or partial-thickness skin loss, devitalized skin, wounds, ulcers, chemical or thermal burns, scars, and full or partial losses or abnormalities of hair, sebaceous glands, or eccrine glands that may be congenital or acquired. Skin injuries are grouped into three categories: epidermal, partial-thickness, and full-thickness. Epidermal injuries do not require specific surgical treatment, as only the epidermis is affected and this regenerates rapidly without scarring. Partial-thickness wounds affect the epidermis and the dermis. Such wounds generally heal by epithelialization from the margins of the wound, where basal keratinocytes from the wound edge, hair follicle, or sweat glands migrate to cover the damaged area. Full-thickness injuries are characterized by the complete destruction of epithelial-regenerative elements. This type of injury heals by contraction, with epithelialization from only the edge of the wound. Partial-thickness injuries and full-thickness injuries often require skin grafting.

The skin substitutes and microspheres of the invention may also be used to treat surgical wounds. For example, the removal of large skin lesions, such as giant nevi (moles), leaves wounds that cannot heal on their own, and are too large for autologous split-thickness skin grafts. The compositions of the invention will be useful for treating such lesions.

The most common form of hair loss is a progressive hair thinning condition called androgenic alopecia. Hair loss can occur on any part of the body and can arise from any number of factors. For example, traction alopecia is most commonly found in people who pull on their hair with excessive force into ponytails or cornrows. Alopecia areata is an autoimmune disorder that can result in hair loss in just one location (alopecia areata monolocularis), or can result in the loss of every hair on the entire body (alopecia areata universalis). Hypothyroidism, tumors, and skin outgrowths (such as cysts) also induce localized baldness. Hair loss can also be caused by chemotherapy, radiation therapy, childbirth, major surgery, poisoning, mycotic infections, and severe stress. In addition, iron deficiency is a common cause of hair thinning. In many cases of hair loss, the hair follicles have stopped cycling and have entered a quiescent stage. In other cases, the hair follicles are lost completely, or never formed in the first place.

The compositions and methods of the invention are useful for treating any condition requiring growth of hair follicles. In one embodiment, the method also induces eccrine glands. In another embodiment, the method further induces sebaceous glands.

b) Administration of Skin Substitutes

In one embodiment, the method comprises grafting to a patient the skin substitute of the invention. The skin substitutes of the invention may be administered by any suitable technique known to those skilled in the art.

(1) Preparation of the Graft Site

The graft site may be prepared by any technique known to those skilled in the art. The graft site may be injured skin (for example, partial- or full-thickness chemical or thermal burns, denuded skin, or devitalized skin), a wound bed with partial or complete absence of skin (for example, a site where the skin was avulsed or ulcerated), a surgical wound (for example, following excision of benign or malignant skin growths), or skin with any congenital (for example, aplasia cutis congenita) or acquired (for example, skin scarred by any cause) reduction, abnormality, or absence of hair follicles, sebaceous glands, and/or eccrine glands. In some embodiments, the graft site is washed with water, an antibiotic wash, or an alcohol solution (such as an alcohol swab). In another embodiment, a desired pattern of hair is drawn on the graft site with a surgical marker. In other embodiments, a local anesthetic is administered to the patient. In cases requiring further anesthetics, a gaseous, intravenous, or nerve block anesthetic may be administered to the patient.

In yet further embodiments, the existing skin tissue, devitalized tissue, eschar, wound or ulcer edges, or scar tissue is removed using standard techniques in the art. When possible, any skin infections or deteriorating conditions should be resolved prior to application of the graft. Antimicrobial, antifungal, and antiviral agents, administered topically or systemically, may be used during a period of time (such as a week) prior to and following administration of the skin substitute to reduce the risk of infection.

Skin substitutes may be applied to a clean, debrided skin surface after thoroughly irrigating the wound with a non-cytotoxic solution. Debridement may extend to healthy, viable, bleeding tissue. Prior to application, hemostasis may be achieved. Prior to debridement the wound may be thoroughly cleansed with sterile saline to remove loose debris and necrotic tissue. Using tissue nippers, a surgical blade, or curette, hyperkeratotic and/or necrotic tissue and debris may be removed from the wound surface. Ulcer margins may be debrided to have a saucer effect. After debridement, the wound may be cleansed thoroughly with sterile saline solution and gently dried with gauze. Oozing or bleeding resulting from debridement or revision of wound edges may be stopped through the use of gentle pressure, or if necessary ligation of vessels, electrocautery, chemical cautery, or laser. Heavy exudation may displace a skin substitute and reduce adherence. Exudation may be minimized by appropriate clinical treatment. For example, sterile air at room temperature or up to 42° C. may be blown over the wound until the wound is sticky. If exudation persists, the skin substitute may be made permeable to exudate by perforating the skin substitute to allow for drainage.

(2) Application of the Skin Substitute

A variety of clinical techniques may be used for applying the skin substitute to the patient. Skin substitutes may be applied in the outpatient clinic or in a surgical suite depending on the size of the defect being repaired, pain level, and the need for general anesthesia. Before applying the skin substitute, the practitioner can review the expiration date of the skin substitute, check the pH, and visually observe and smell the skin substitute to ensure that there are no contaminants, such as bacterial contaminants or particulate matter. The skin substitute may be stored in a polyethylene bag at controlled temperature 68° F.-73° F. (20° C.-23° C.) until immediately prior to use.

The practitioner may cut open the sealed polyethylene bag, and if the skin substitute is provided in a cell culture dish or plastic tray, it may be transferred to the sterile field with aseptic technique. If present, a tray or cell culture dish lid may be lifted off, and the practitioner may note the epidermal and dermal layer orientation of the skin substitute. Using a sterile atraumatic instrument, a practitioner may gently dislodge approximately 0.5 inch of the skin substitute away from the wall of the tray or cell culture dish. When lifting the skin substitute, a practitioner may be careful not to perforate or lift any membrane beneath the skin substitute, which, if present, should remain in the tray.

With sterile gloved hands, a practitioner may insert one index finger under the released section of the skin substitute and use the other index finger to grasp the skin substitute in a second spot along the edge of the device. Holding the skin substitute in two places, the practitioner may lift the entire skin substitute out of the tray or cell culture dish using a smooth, even motion. If excessive folding occurs, the skin substitute can be floated (epidermal surface up) onto warm sterile saline solution in a sterile tray.

The skin substitute may be placed so that the dermal layer (the glossy layer closest to the medium) is in direct contact with the site for the skin substitute.

Using a saline moistened cotton applicator, the practitioner may smooth the skin substitute onto the site so there are no air bubbles or wrinkled edges. If the skin substitute is larger than the site for application, the excess skin substitute may be trimmed away to prevent it from adhering to the dressing. If the skin substitute is smaller than the site for application, multiple skin substitutes may be applied adjacent to each other until the defect is filled.

The skin substitute may be secured with any appropriate clinical dressing. Sutures or samples are not required but may be used in some instances to anchor the graft to the graft bed. Dressings may be used to assure contact of the skin substitute to the site for application and to prevent movement. Therapeutic compression may be applied to the graft site. In some cases it may be necessary to immobilize the grafted limb to minimize shearing forces between the skin substitute and the application site. Dressings may be changed once a week or more frequently if necessary.

Additional applications of skin substitutes may be necessary in certain instances. Prior to additional applications, non-adherent remnants of a prior skin graft or skin substitute should be gently removed. Healing tissue or adherent skin substitutes may be left in place. The site may be cleansed with a non-cytotoxic solution prior to additional applications of skin substitute. In one embodiment, an additional skin substitute may be applied to the areas where the prior skin substitute is not adherent.

c) Injection of Trichogenic Cells

The trichogenic cells of the invention may be injected by any suitable method known to those skilled in the art. In one embodiment, the method comprises subdermally or intradermally delivering to a patient trichogenic cells. In another embodiment, the method further comprises delivering epithelial cells to the patient. Cells may be delivered as a suspension, cluster, aggregate, or in combination with biodegradable microspheres. When injecting a suspension, each injection site may deliver 50-2,000 cells. When injecting cells in combination with biodegradable microspheres, each injection site may deliver one or more such combination.

(1) Preparation of the Graft Site

The graft site may be washed with water, an antibiotic wash, or an alcohol solution (such as an alcohol swab). In another embodiment, a desired pattern of hair may be drawn on the graft site with a surgical marker, either in an outline fashion or a pixilated fashion showing each injection site. Paper templates or templates of other material may also be applied to the injection site showing the pattern for injection, or injections may be delivered at the correct spacing by using robotics or a device with multiple injection ports in a grid. In other embodiments, a local anesthetic may be administered to the patient. In cases requiring further anesthetics, a gaseous, intravenous, or nerve block anesthetic may be administered to the patient.

(2) Injection Methods, Dosage, and Frequency of Administration

The injections may be administered according to techniques known in the art for subdermal or intradermal injections. A concentration of 1,000 to 20,000 cells/ml may be used in the injection. A volume of 0.05 to 0.1 ml may be injected at each injection site using a 1-3 ml syringe with a 14-30 gauge needle. In such embodiments, the skin is pulled taut, and the needle is inserted bevel up at a 5° to 30° angle with the skin. The cells are then injected slowly with gentle pressure, the needle is removed, and gentle pressure is applied to prevent leakage and promote absorption.

Injections may be repeated over a period of time, either for patient comfort or because additional hair follicles may be produced after repeated administration. In such a case, the administrations may be spaced a week apart, two weeks, three weeks, a month, two months, three months, or six months apart.

Several of the foregoing embodiments are illustrated in the non-limiting examples set forth below. However, other embodiments of the invention will be apparent to those skilled in the art from consideration of the specification and practice of the invention disclosed herein. It is intended that the specification and examples be considered as exemplary only and are not restrictive of the invention, as claimed. In addition, all references cited herein are to be considered incorporated by reference in their entirety.

EXAMPLES

Example 1

Human DP cells isolated from temporal scalp dermis (Promocell, Heidelberg, Germany) from one male and five female donors were propagated in vitro according to methods described below. Alkaline phosphatase activity, a DP marker which correlates with hair-inducing capacity (Ohyama et al., 2013), was measured in vitro using the BCIP/NBT substrate (Sigma-Aldrich, St. Louis, Mo.) on passage 5 DP cells. To screen for trichogenicity, the reconstitution described in Zheng et al., 2005, and Kang et al., 2012 was used with minor modifications.

Figure 2:
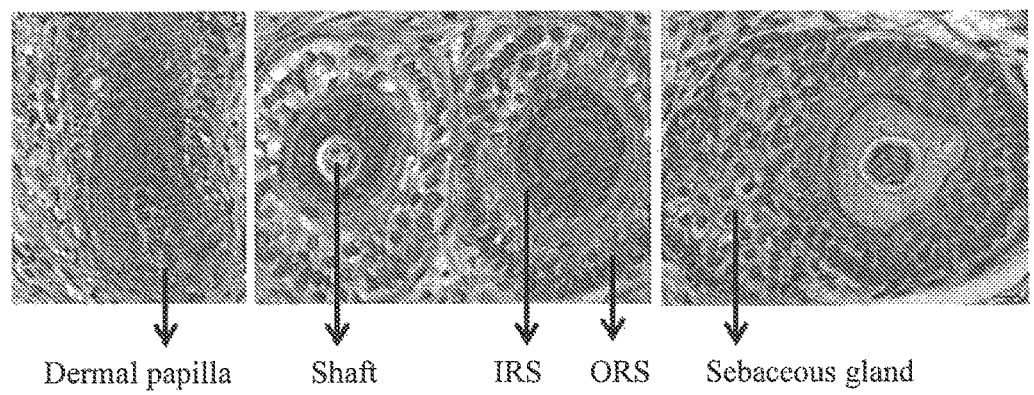
FIG. 2 shows that pilosebaceous units formed by grafting a skin substitute comprising human neonatal foreskin keratinocytes, human dermal papilla cells, and type I collagen are complete with dermal papillae, hair shafts, inner root sheaths (IRS), outer root sheaths (ORS), and sebaceous glands.
Figure 3A:
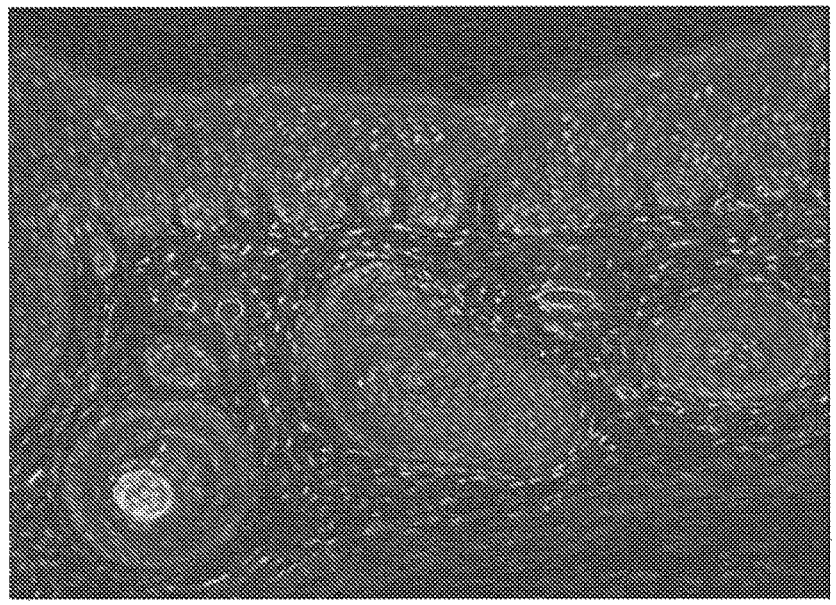
FIG. 3A shows the hybridization of a fluorescein-labeled oligonucleotide probe for human Alu DNA to grafts containing hair follicles formed by grafting a skin substitute comprising human neonatal foreskin keratinocytes, human dermal papilla cells, and type I collagen. Positive signal (green) in the hair follicles indicates that the cells are of human origin.
Figure 3B:
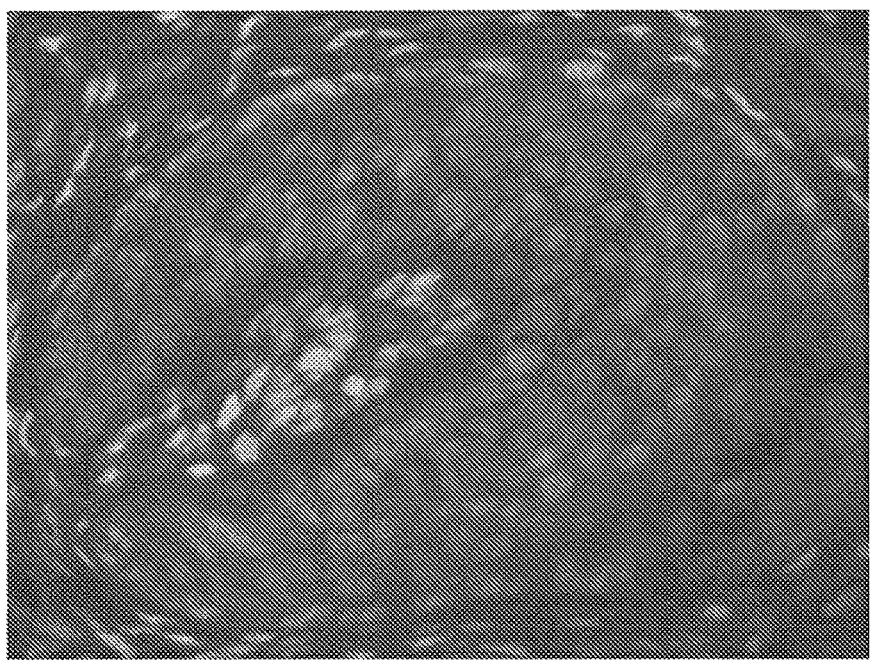
FIG. 3B shows a dermal papilla formed by grafting a skin substitute comprising human neonatal foreskin keratinocytes, human dermal papilla cells, and type I collagen, hybridized with the fluorescein-labeled oligonucleotide probe for human Alu DNA. Positive signal indicates that the dermal papilla is composed of cells of human origin.
Figure 4:
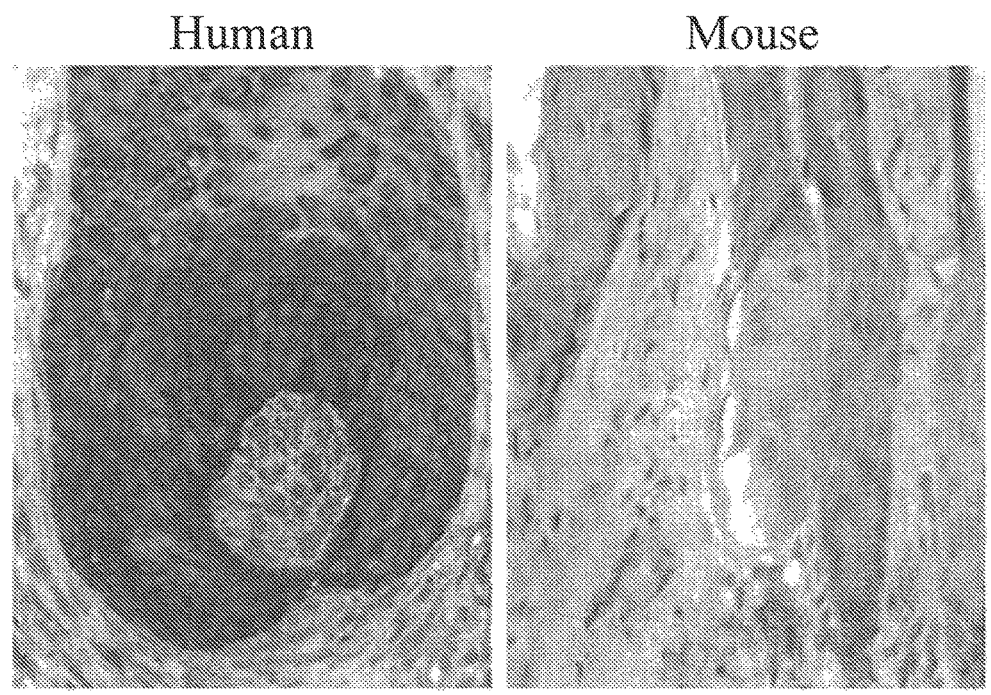
FIG. 4 shows hair follicles formed by grafting a skin substitute comprising human neonatal foreskin keratinocytes, human dermal papilla cells, and type I collagen, stained with an antibody that recognizes human COX IV. Positive staining (red) in both epithelial and mesenchymal cells (left) indicates that both are derived from the human cells contained within the graft. No staining is seen in mouse follicles (right).
Figure 5:
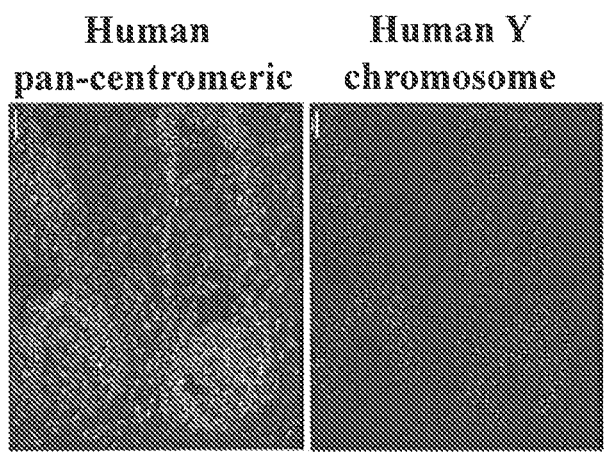
FIGS. 5A and 5B show that the dermal papilla niche in the graft formed by a skin substitute comprising human neonatal foreskin keratinocytes, human dermal papilla cells, and type I collagen is formed from the dermal papilla cells.
Figure 7:
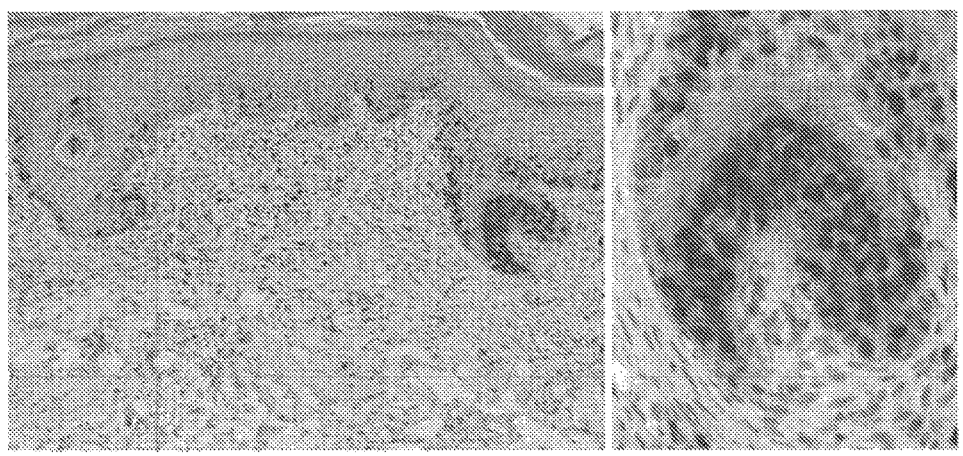
FIG. 7 shows that proliferating cells in the graft formed by a skin substitute comprising human neonatal foreskin keratinocytes, human dermal papilla cells, and type I collagen are scattered in the basal layer of the epidermis and dense in the hair follicle matrix. Red staining shows immunoreactivity against Ki-67, a marker of cell proliferation.
Figure 9:
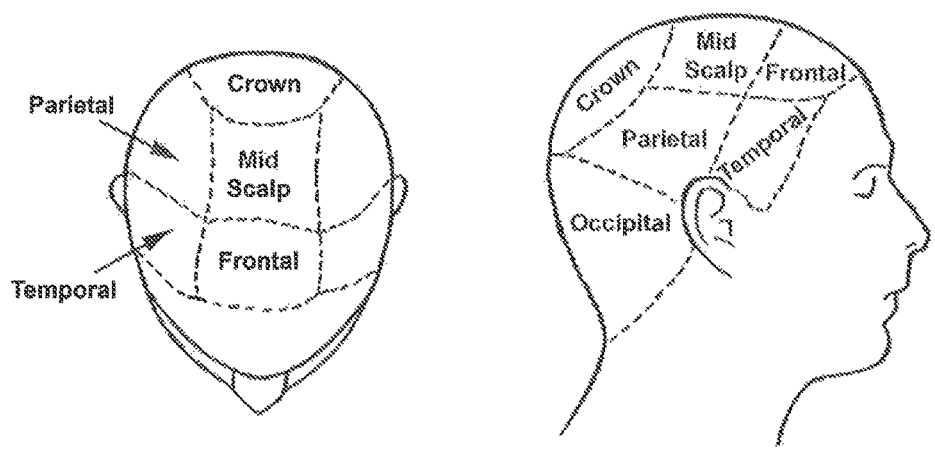
FIG. 9 shows a schematic of certain regions of the scalp.
Figure 10:
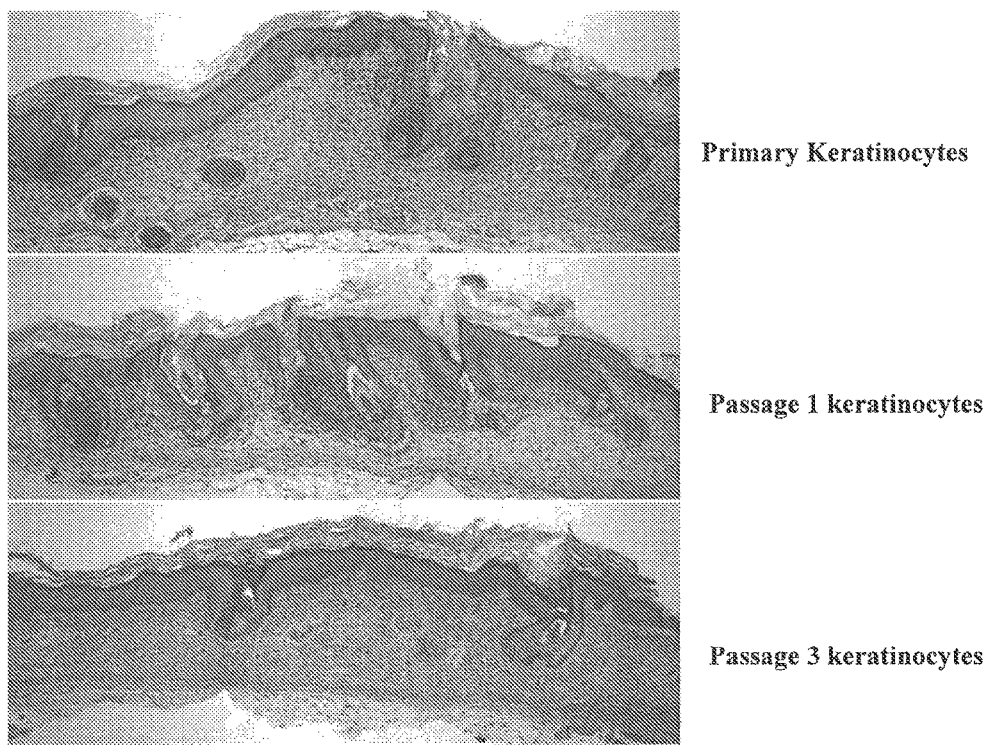
FIG. 10 shows hair follicles in the grafts made with HDP47 and three different passages of keratinocytes (p0 (top), p1 (middle), and p3 (bottom)). Primary or P1 keratinocytes form more hair follicles than P3 keratinocytes.
Figure 12:
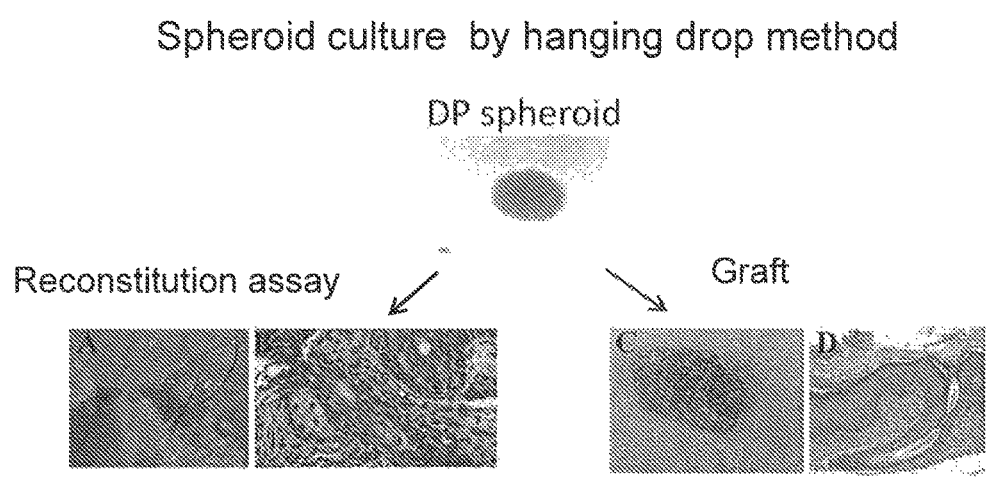
FIG. 12 shows that dermal papilla microspheres augment HF formation in both reconstitution assays and in skin grafts. The bottom left two images show human DP spheroids induce chimeric HFs in reconstitution assay. Hair fibers are seen in the hypodermis 4 weeks following injection of a mixture of human DP spheroids and mouse epidermal cells (left-most image). Human DP 2D cultures do not induce HF. H&E stained horizontal section of injection cyst forming HFs and sebaceous glands (second image from left). The bottom right two images show that human DP spheroids induce human HFs in a reconstitution assay. Appearance of graft, 8 weeks after grafting on the back of a nude mouse, is shown in the first of the two images. A representative H&E stained graft section showing hair follicle with hair shaft is provided in the right-most image.

Human DP cells induced HFs when grown as spheroids, but not as monolayers, when coinjected with mouse epidermal aggregates in a reconstitution assay (Table 1), similar to the results of others (Kang et al, 2012). Skin substitutes (of which DECs are one type) constructed with human DP cells and human neonatal foreskin keratinocytes (NFKs) were grafted onto female nude mice. Eight weeks after grafting, HFs were observed in mice grafted with human DP cells that had high but not low alkaline phosphatase activity (Table 1, FIG. 1A). HFs had a bulb, dermal sheath, hair matrix and cortex (FIG. 2). Epithelial compartments of the HFs were intact with concentric layers of inner and outer root sheaths, hair shaft and sebaceous glands (FIG. 2). Fluorescence in situ hybridization (FISH) using a probe for human-specific Alu repetitive sequences (green) hybridized to the nuclei of both epithelial and dermal components of the HF confirming their human origin (FIG. 3A-3B). An antibody reactive with human but not mouse COX IV stained follicular epithelium and dermal fibroblasts of grafts (FIG. 4). FISH using a human-specific, pan-centromeric probe (green) hybridized to the nuclei of both epithelial and dermal components (FIG. 5A), whereas a human-specific Y-chromosome probe (red) hybridized to nuclei in the epidermis and the follicular epithelium, consistent with the origin of dermal and epidermal cells from female and male donors, respectively (FIG. 5B). HFs also stained for markers of specific compartments of a fully developed human HF. Cells in the region of the DP and lower DS displayed alkaline phosphatase activity (FIG. 6A), normal reactivity with specific antibodies to human nestin (FIG. 6B) and versican (FIG. 6C). As expected, HFs in anagen phase HFs had more concentrated immunoreactivity to Ki-67 in the region of the hair matrix relative to the overlying epidermis (FIG. 7). The companion layer as identified by keratin 75 staining was present between the inner and outer root sheaths (FIG. 8B). The basal layer of the outer root sheath was immunoreactive for Keratin 15, a marker of HF stem cells located in the bulge region (FIG. 8A).

These experiments show that human mesencymal cells such as DP cells can induce complete pilosebaceous units (i.e., complete hair follicle growth or complete hair follicle neogenesis) in vivo.

mixture of DMEM and Ham's F12 (3:1) (GIBCO/Invitrogen, Grand Island, N.Y.) containing 0.1% FBS, after which the keratinocytes were brought to the air-liquid interface and cultured in a mixture of DMEM and Ham's F12 (3:1) containing 1% FBS for another 2 days before grafting.

Microspheres:

Cell Clusters: Cell aggregates for injection were formed using the hanging droplet method. (Qiao J. et al., "Hair follicle neogenesis induced by cultured human scalp dermal papilla cells," Regen Med 4(5): 667-76 (2009).) Briefly, a mixture of human mesenchymal cells and keratinocytes (10:1, 5:1, 1:1, 1:5 or 1:10) was suspended in Dermal Papilla Medium (Promocell). The cells were applied in 10-μl droplets (each droplet contains either $1 \times 10^4$ or $0.5 \times 10^4$ cells) in the lid of a 100-mm petri dish oriented so that droplets were hanging upside down. 10 ml of phosphate buffered saline was placed in the bottom of the petri dish. The suspended droplets were incubated in a 37° C., 5% $CO_2$ incubator. Aggregate formation was completed within 18-20 h, and the reconstitution assay was performed 48 hours after seeding. An alternative approach is to use Chang medium containing 0.24% methylcellulose. The cells were applied in 20-μl droplets (each droplet contains $4 \times 10^4$ cells) in the bottom of a 100-mm petri dish. The petri dish was inverted such that the droplets were hanging upside down. The suspended droplets were incubated in a 37° C., 5% $CO_2$ incubator. Aggregate formation was completed within 18-20 h. Upon formation, aggregates were transferred individually to wells of a 96-well round-bottom assay plate containing 150 μl Chang medium. The wells were precoated with 0.24% methylcellulose medium to prevent adherence of protohairs. The culture medium was changed every 2-3 days.

Optional Addition of Biodegradable Microspheres: Biodegradable microspheres for injection may be fabricated from 75:25 PLGA (molecular weight=100,000 Da, Birmingham Polymers, Birmingham, Ala.) using a conventional oil/water emulsion and solvent evaporation/extraction method. For example, 600 mg PLGA may be dissolved in 12 ml of methylene chloride, added to 400 ml aqueous solution of 0.5% (w/v) polyvinyl alcohol (molecular weight=30,000-

TABLE 1

Evaluation of trichogenicity of human dermal papilla (DP) cells

|  | HDP47 | HDP44 | HDP41 | HDP43 | HDP60 | HDP52 |
|---|---|---|---|---|---|---|
| Hair follicle formation in reconstitution assay | 5/5 | 2/2 | 2/2 | 2/2 | 2/2 | 2/3 |
| Number of grafts with hair follicles/total number of grafts in dermal-epidermal composites | 9/11 | 6/6 | 4/5 | 0/6 | 0/4 | 0/5 |
| Percent cells positive for alkaline phosphatase activity (n = 6, Mean ± SD) | 75 ± 3 | 67 ± 3 | 52 ± 4 | 35 ± 1 | 29 ± 4 | 17 ± 4 |

Preparation of Cells for Grafting

Skin Substitutes: Three-dimensional in vitro constructs were prepared for grafting using established methods modified as described herein. Briefly, human dermal papilla cells were mixed with 1 mg/ml type I collagen (rat) (in other embodiments, the collagen could be bovine) in 10% FBS/DMEM, and added to 6 well transwell plates (Corning Incorporated, Corning, N.Y.) at a density of $1.5 \times 10^5$ cells per $cm^2$. The dermal equivalents were cultured in 10% FBS/DMEM for 4 days before aliquoting $1 \times 10^6$ keratinocytes on top. The constructs were cultured submerged for 2 days in a 70,000 Da, Sigma), and stirred vigorously at room temperature overnight. The microspheres may be collected by centrifugation, washed three times with distilled water, and strained to a size of 50-200 μm in diameter. The microspheres may be lyophilized and sterilized with ultraviolet light for 6 hours. Human mesenchymal cells ($2.5 \times 10^7$ cells) and keratinocytes ($6 \times 10^6$ cells) may be placed with PLGA microspheres (1 μg microspheres/$10^5$ cells) in a spinner flask (Bellco Glass Inc., Vineland, N.J.) containing 30 ml of serum-free KGM containing 10 ng/ml of EGF for keratinocytes, or DMEM/F12 containing 10% (v/v) FBS for mesenchymal cells, and cultured at 50 rpm for 2 weeks. The medium may be exchanged every other day. Cell aggregates may be allowed to settle down, 16 ml of the culture supernatant may be collected and centrifuged, 15 ml of the supernatant may be removed, and 15 ml of fresh medium may be added to the centrifuged cells in 1 ml of remaining supernatant. The cells in fresh medium may be transferred to the spinner flasks. Alternatively, clusters of cells may be formed by suspending the cells in sodium alginate and then forming spherical droplets using a high-voltage electric droplet generator as described in Lin C. M. et al., "Microencapsulated human hair dermal papilla cells: a substitute for dermal papilla?," Arch Dermatol Res. 300(9):531-5 (2008).

Grafting Process

Placement of Composite: Mice were grafted in a horizontal laminar flow hood using 6-8 week old female Cr:NIH (S)-nu/nu mice (FCRDC, Frederick, Md.) anesthetized using inhalant anesthesia with a mixture of $O_2$ and isoflurane (2-4%). The grafting area on back of the mouse was carefully estimated, and skin was removed using curved scissors after washing with povidine and 70% ethanol. Skin substitutes were placed on the graft bed in correct anatomical orientation, covered with sterile petroleum jelly gauze, and secured with bandages. The mice were transferred back to the sterile cages after reawakening. The bandages were changed at 2 weeks and removed after 4 weeks. Mice are sacrificed 4-18 weeks after grafting.

Injection of Cells: Cells were directly injected into mouse skin using a technique similar to that described in Ortiz-Urda et al. For injection of human mesenchymal cells into mouse skin, 6-8 week old female Cr:NIH(S)-nu/nu mice (FCRDC, MD) were injected hypodermally with a mixture of DP cells (1 million cells/patch; either dissociated DP cells from monolayer cultures or DP spheroids), and 100,000 epidermal aggregates (1 million cells) isolated from 0-2 day old C57B1/6 neonatal mice skin (Charles River, N.C.), using a 25-gauge needle. Injected cells were in a medium consisting of 1:1 mixture of DMEM and F12. The injection was performed by first piercing the skin, then directing the needle back upward toward the surface and injecting the cells as superficially as possible. This led to the formation of a well-demarcated papule in the center of the injected area. Positive controls received 1 million dermal cells isolated from the same C57B1/6 mice skin and 50,000 epidermal aggregates. 2 to 4 weeks post implantation HF formation was analyzed on the injection site by dissecting and viewing ventral side of the patch skin microscopically.

Implantation of Cells: After anesthetizing, small incisions approximately 0.5-1.0 mm in width and length may be made using a 27-gauge needle. A single cultured aggregate (protohair) may be inserted at a shallow position within each incision. Following insertion, incisions may be left to heal.

After the animal is anesthetized, full-thickness skin wounds (1.5×1.5 $cm^2$ rectangular shape) may be created on the transplantation area. To minimize the migration of host skin cells from the wound margins and spontaneous wound contraction, the skin at the wound margins may be burned using a cautery and fixed to adjacent muscle layers with nonresorbable 5-0 nylon sutures (AILEE Co., Pusan, Korea). Mesenchymal cells (approximately $10^8$ cells/wound) and keratinocytes (approximately 7.5×$10^6$ cells/wound) cultured on PLGA microspheres may be transplanted to the wounds using a 1-mL syringe without a needle. After transplantation, the wounds may be dressed with dressing materials, Tegaderm (3M Health Care, St. Paul, Minn.) and sterile cotton gauze, and firmly fixed using Coban, a self-adhesive wrap (3M Health Care). An antibiotic (Cefazolin, 0.1 mg/mouse, Yuhan Co., Seoul, Korea) and an analgesic (Buprenorphine, 0.1 mg/kg, Hanlim Pharm Co., Seoul, Korea) may be administered intramuscularly and subcutaneously, respectively, for 5 days after transplantation. The mice may be housed singly after surgery and receive humane care in compliance with the guidelines for the care and use of laboratory animals of NIH.

Example 2

Studies were done using human dermal papilla cells grown from the temporal scalp of 6 individuals (HDP47, HDP44, HDP41, HDP43, HDP60, and HDP52) and human dermal papilla cells grown from the occipital scalp from 7 individuals (1-7). All cells were combined with human foreskin keratinocytes and rat collagen type I as described as in Example 1. The alkaline phosphatase activity of cells was measured in monolayer cultures before grafting.

Table 2 shows the results of the grafting experiments comparing human dermal papilla cells isolated from the temporal versus occipital scalp.

The second column in Table 2 shows the number of grafts in which the epidermis showed a typical human epidermal morphology by H&E staining. Dermal papilla cells from the temporal scalp supported the development of the human keratinocytes into a stratified squamous epithelium much better than those from the occipital scalp. In many grafts with occipital dermal papilla cells, the mouse keratinocytes from the borders of the graft migrated in and replaced the human keratinocytes.

The third column in Table 2 indicates the number of grafts with hair follicles. Human hair follicles formed using dermal papilla cells from 3/6 donors from the temporal scalp, but none from the occipital scalp. Hair follicles were observed in at least 80% of grafts using dermal papilla cells from 3 patients, including 19 out of 22 grafts from the trichogenic samples. No hair follicles were observed in grafts using dermal papilla cells from the occipital scalp. The data in parentheses indicates that there was no evidence for the formation of chimeric hair follicles (no induction of hair follicles by the dermal papilla cells in mouse keratinocytes overlying the graft).

Hair follicle formation was observed in those with higher alkaline phosphatase activity. This is one potential explanation for the lack of hair follicle formation in the dermal papilla samples from the occipital scalp. The other possible explanation is differing embryonic origins of the dermal papilla cells from temporal scalp (neural crest derived) as compared to occipital scalp (mesoderm derived).

TABLE 2

Evaluation of trichogenicity of human dermal papilla (DP) cells from temporal vs. occipital scalp

| Harvest site for DP cells | Number of grafts with human epidermal morphology/ total number of mice grafted | Number of grafts with hair follicles/total number of grafts with human epidermal morphology | Percent cells positive for alkaline phosphatase activity (Mean ± SD, n = 6) |
|---|---|---|---|
| Temporal | | | |
| HDP47 | 9/18 | 9/11 | 75 ± 3 |
| HDP44 | 6/6 | 6/6 | 67 ± 3 |
| HDP41 | 4/6 | 4/5 | 52 ± 4 |
| HDP43 | 6/12 | 0/6 | 35 ± 1 |

TABLE 2-continued

Evaluation of trichogenicity of human dermal papilla (DP) cells from temporal vs. occipital scalp

| Harvest site for DP cells | Number of grafts with human epidermal morphology/ total number of mice grafted | Number of grafts with hair follicles/total number of grafts with human epidermal morphology | Percent cells positive for alkaline phosphatase activity (Mean ± SD, n = 6) |
|---|---|---|---|
| HDP60 | 4/6 | 0/4 | 29 ± 4 |
| HDP52 Occipital | 5/6 | 0/5 | 17 ± 4 |
| 1 | 0/5 | 0/5 | — |
| 2 | 1/5 | 0/1 | — |
| 3 | 0/6 | 0/6 | 42 ± 8 |
| 4 | 0/6 | 0/6 | 21 ± 3 |
| 5 | 3/6 | 0/3 | 34 ± 5 |
| 6 | 0/6 | 0/6 | 39 ± 7 |
| 7 | 0/6 | 0/6 | — |

Example 3

Figure 13:
FIG. 13 is an H&E stain showing a hair shaft emerging from the infundibulum of a human hair follicle in a dermal-epidermal composite construct 8 weeks after grafting.
Figure 14:
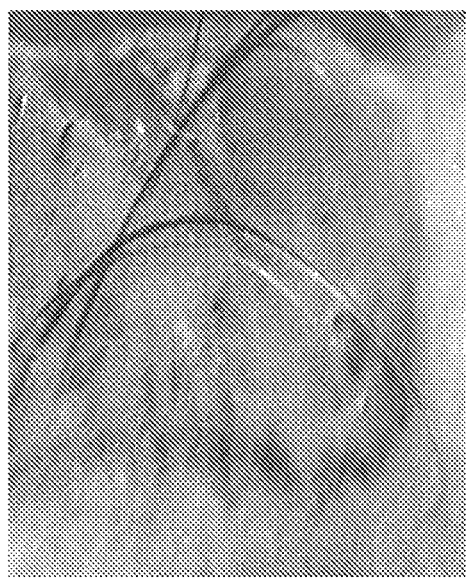
FIG. 14 is a dermal-epidermal composite (dermal papilla cells from temporal scalp dermis and neonatal foreskin keratinocytes) photographed under a dissection microscope after 10 weeks.
Figures 15A, 15B:
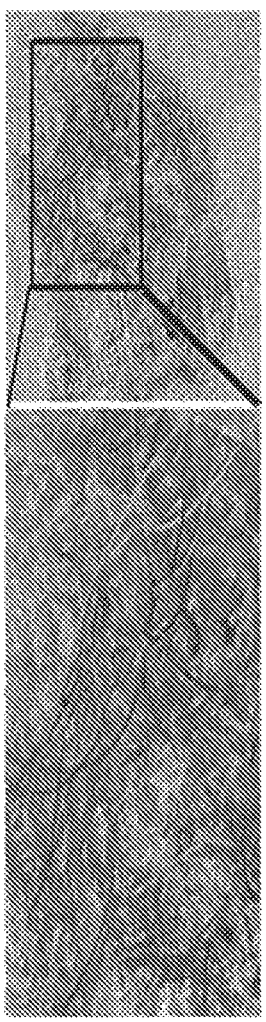
FIG. 15A shows a representative dermal-epidermal composite graft with hair shafts visible 12 weeks after grafting, while FIG. 15B provides a magnified view showing the presence of pigmented hair shafts.

Grafted dermal-epidermal composites constructed from human dermal and epidermal cells (neural crest-derived human dermal papilla cells from temporal scalp dermis and neonatal foreskin epidermal cells) were evaluated 8, 12, and 15 weeks after grafting into nude mice. FIG. 13 provides H&E stain showing a hair shaft emerging from the infundibulum of a human hair follicle in a construct 8 weeks after grafting. FIG. 14 is a dermal-epidermal composite photographed under a light microscope after 10 weeks. Hair shafts can be seen emerging from the grafted region. FIG. 15A provides a representative graft with hair shafts visible 12 weeks after grafting, while FIG. 15B provides a magnified view showing the presence of pigmented hair shafts.

FIGS. 16A-C show that different hair follicle stages could be detected in grafts after 15 weeks. The grafts containing dermal papilla cells grown in monolayers, and those grown as spheroids, had telogen hair follicles, confirmed by club-like appearance and spiky keratin fibers (see FIG. 16A), secondary hair germ with adjacent hair papilla (see FIG. 16B, arrow), and a cornified club (see FIG. 16C, negative for toluidine blue staining, arrow). Telogen hair follicles showed no Ki-67 positive cells, consistent with telogen stage of hair follicle (FIG. 17A, arrow). An anagen hair follicle (FIG. 17B, arrow) with dermal papilla from the same section as the telogen hair follicle shows dense Ki-67 reactivity in matrix, as expected.

Figures 18A, 18B:
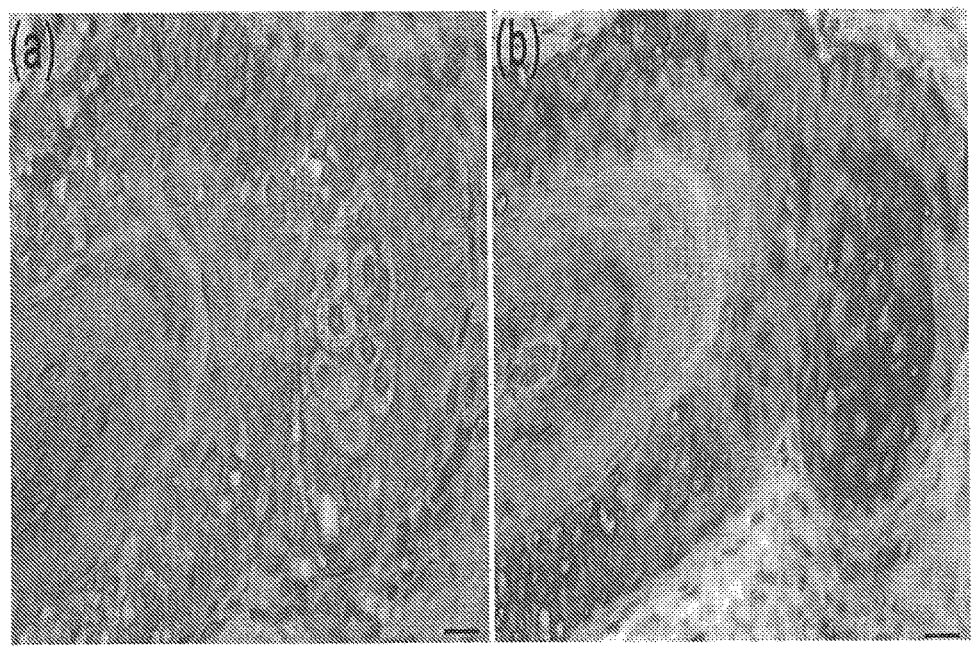
FIGS. 18A and 18B.

Other features of normal hair follicles were seen in composite grafts following grafting. For instance, FIG. 18A shows a representative H&E stained section of a graft that was harvested after 8 weeks, with hair follicle inner and outer root sheath and sebaceous gland visible. FIG. 18B shows that the sebaceous gland was highly immunoreactive to an antibody for cathelicidin, an antimicrobial peptide.

Graft characteristics were evaluated as a function of the type of keratinocytes used in the dermal-epidermal composite, which were constructed from neural crest derived human dermal papilla and neonatal foreskin epidermal cells, and grafted into nude mice. The effects of primary, first passage, and third passage human keratinocyte cultures are shown in Table 3.

TABLE 3

| | Keratinocyte Passage | | |
|---|---|---|---|
| Graft characteristics and skin barrier functions[1, 2] | Primary (P0) | Passage 1 (P1) | Passage 3 (P3) |
| Graft diameter in mm, 4 weeks[+] | 6.0 ± 1.4 | 6.5 ± 1.0 | 6.4 ± 1.9 |
| Graft diameter in mm[++] | 5.8 ± 1.2 | 5.5 ± 1.1 | 4.4 ± 1.6 |
| Hair follicles/mm of epidermis[++] | 0.9 ± 0.5 | 0.8 ± 0.6 | 0.2 ± 0.2* |
| Epidermal thickness in μm[++] | 127 ± 14 | 117 ± 13 | 89 ± 12*** |
| Follicular area/dermal area in percentage[++] | 16 ± 12 | 12 ± 9 | 4 ± 3 |
| Hair follicle diameter in μm[^] | 250 ± 38** | 144 ± 27 | 107 ± 22 |
| Shaft diameter in μm[^^] | 45 ± 13 | 21 ± 3* | 24 ± 8 |
| Transepidermal water loss in g/m$^2$h[#] | 27 ± 8 | 29 ± 6 | 34 ± 15 |
| Water Content[#] | 24 ± 6 | 21 ± 8 | 18 ± 9 |
| Surface Hydration[##] | 3 ± 4 | 7 ± 2 | 4 ± 3 |

All measurements in Table 3 were taken at 8 weeks unless indicated otherwise in the table (footnote 1). All results are expressed as mean+/−standard deviation (footnote 2). Other asterisks and notes from the table are explained below.
[+] Number of grafts evaluated: P0, n=8; P1, n=7; P3, n=8.
[++] Number of grafts evaluated: P0, n=6; P1, n=6; P3, n=7.
[^] Number of grafts evaluated: P0, n=5; P1, n=5; P3, n=3.
[^^] Number of grafts evaluated: P0, n=3; P1, n=3 P3, n=2.
[#] Number of grafts evaluated: P0, n=6; P1, n=6; P3, n=5.
[##] Number of grafts evaluated: P0, n=3; P1, n=5; P3, n=4.
* Significantly less than primary keratinocytes, p<0.05.
*** Significantly less than primary and passage 1 keratinocytes, p<0.005.
** Significantly greater than passaged keratinocytes, p<0.02.

What is claimed is:

1. A skin substitute comprising, in a suspension,
   (i) epithelial cells; and
   (ii) isolated mesenchymal cells that are derived from the temporal region of a scalp, wherein the skin substitute induces hair follicle neogenesis.

2. The skin substitute of claim 1, wherein the skin substitute is provided in a microsphere.

3. The skin substitute of claim 1, wherein the suspension comprises a matrix.

4. The skin substitute of claim 3, wherein the matrix is a collagen matrix.

5. The skin substitute of claim 1, wherein the isolated mesenchymal cells are hair follicle dermal cells.

6. The skin substitute of claim 5, wherein the hair follicle dermal cells are neural crest-derived cells, dermal papilla cells, or dermal sheath cells.

7. The skin substitute of claim 1, wherein the epithelial cells are keratinocytes.

8. The skin substitute of claim 1, wherein the epithelial cells are from a first or second passage and/or the isolated mesenchymal cells are from a first, second, third, or fourth passage.

9. The skin substitute of claim 1, wherein the epithelial cells and the isolated mesenchymal cells are passaged in keratinocyte-conditioned medium.

10. The skin substitute of claim 1, wherein the epithelial cells and the isolated mesenchymal cells are human.

11. The skin substitute of claim 1, wherein the isolated mesenchymal cells are genetically unmodified mesenchymal cells.

12. A method for inducing hair follicle neogenesis, comprising delivering the skin substitute of claim 1 to a human subject, wherein the human subject has partial-thickness skin loss, full-thickness skin loss, a wound, a burn, a scar, or hair loss.

* * * * *